(12) United States Patent
Ou et al.

(10) Patent No.: US 11,197,666 B2
(45) Date of Patent: Dec. 14, 2021

(54) SURGICAL COATED NEEDLES

(71) Applicant: Ethicon LLC, Guaynabo, PR (US)

(72) Inventors: Duan Li Ou, Warren, NJ (US); Frank Cichocki, Easton, PA (US); Thien Nguyen, Flowery Branch, GA (US)

(73) Assignee: Cilag GmbH International, Zug (CH)

( * ) Notice: Subject to any disclaimer, the term of this patent is extended or adjusted under 35 U.S.C. 154(b) by 43 days.

(21) Appl. No.: 16/053,221

(22) Filed: Aug. 2, 2018

(65) Prior Publication Data

US 2019/0083093 A1 Mar. 21, 2019

Related U.S. Application Data

(60) Provisional application No. 62/559,267, filed on Sep. 15, 2017.

(51) Int. Cl.
| | | |
|---|---|---|
| *A61B 17/06* | (2006.01) | |
| *B05D 1/02* | (2006.01) | |
| *B05D 1/18* | (2006.01) | |
| *B05D 3/06* | (2006.01) | |
| B05D 5/08 | (2006.01) | |
| B05D 7/00 | (2006.01) | |
| B23K 26/382 | (2014.01) | |
| B05D 7/14 | (2006.01) | |
| A61B 17/00 | (2006.01) | |
| B05D 3/04 | (2006.01) | |

(52) U.S. Cl.
CPC .......... *A61B 17/06066* (2013.01); *B05D 1/02* (2013.01); *B05D 1/18* (2013.01); *B05D 3/06* (2013.01); *A61B 2017/00526* (2013.01); *A61B 2017/00849* (2013.01); *A61B 2017/00853* (2013.01); *A61B 2017/06028* (2013.01); *B05D 3/0493* (2013.01); *B05D 5/08* (2013.01); *B05D 7/14* (2013.01); *B05D 7/50* (2013.01); *B05D 2258/00* (2013.01); *B23K 26/389* (2015.10)

(58) Field of Classification Search
CPC .... A61B 17/06066; A61B 2017/00526; A61B 2017/00849; A61B 2017/06028; B05D 1/02; B05D 1/18
USPC ........................................................ 427/2.28
See application file for complete search history.

(56) References Cited

U.S. PATENT DOCUMENTS

| | | |
|---|---|---|
| 1,944,823 A | 1/1934 | Lament |
| 4,256,870 A | 3/1981 | Eckberg |
| 4,720,521 A | 1/1988 | Spielvogel et al. |

(Continued)

FOREIGN PATENT DOCUMENTS

| | | |
|---|---|---|
| CA | 2504258 A1 | 10/2005 |
| EP | 0500229 A1 | 8/1992 |

(Continued)

OTHER PUBLICATIONS

R1, ProTech Instruments Trays—Wire Baskets, 2011, Healthmark Industries, https://www.hmark.com/protechwirebakets.php (Year: 2011).*

(Continued)

*Primary Examiner* — Dah-Wei D. Yuan
*Assistant Examiner* — Andrew J Bowman
(74) *Attorney, Agent, or Firm* — Mintz Levin Cohn Ferris Glovsky and Popeo, P.C.

(57) ABSTRACT

Systems and methods for coating surgical needles are provided.

19 Claims, 12 Drawing Sheets
(1 of 12 Drawing Sheet(s) Filed in Color)

(56) References Cited

U.S. PATENT DOCUMENTS

| | | | |
|---|---|---|---|
| 4,806,430 A | 2/1989 | Spielvogel et al. | |
| 5,258,013 A * | 11/1993 | Granger | A61B 17/06066 |
| | | | 427/372.2 |
| 5,447,465 A * | 9/1995 | Samsel | A61B 17/06 |
| | | | 451/32 |
| 5,458,616 A | 10/1995 | Granger et al. | |
| 5,463,010 A | 10/1995 | Hu et al. | |
| 5,536,582 A | 7/1996 | Prasad et al. | |
| 5,645,884 A | 7/1997 | Harlow, Jr. et al. | |
| 5,688,598 A | 11/1997 | Keck et al. | |
| 5,911,711 A | 6/1999 | Pelkey | |
| 5,985,355 A | 11/1999 | Walther et al. | |
| 5,997,517 A | 12/1999 | Whitbourne | |
| 6,018,860 A | 2/2000 | Smith et al. | |
| 6,053,977 A | 4/2000 | Konishi | |
| 6,231,990 B1 | 5/2001 | Lin et al. | |
| 6,252,195 B1 | 6/2001 | Mosavi et al. | |
| 6,265,016 B1 | 7/2001 | Hostettler et al. | |
| 6,306,176 B1 | 10/2001 | Whitbourne | |
| 6,325,853 B1 | 12/2001 | Hogan et al. | |
| 6,335,383 B1 | 1/2002 | Scopelianos et al. | |
| 6,558,409 B1 | 5/2003 | Roby | |
| 6,656,167 B2 | 12/2003 | Numao et al. | |
| 6,936,297 B2 | 8/2005 | Roby et al. | |
| 7,015,262 B2 | 3/2006 | Leong | |
| 7,028,867 B2 | 4/2006 | Acum et al. | |
| 7,354,628 B2 | 4/2008 | Steube | |
| 9,332,982 B2 | 5/2016 | Maurer et al. | |
| 10,004,494 B2 | 6/2018 | Maurer et al. | |
| 2001/0027299 A1 | 10/2001 | Yang et al. | |
| 2004/0040467 A1 | 3/2004 | Thomas et al. | |
| 2004/0071988 A1 | 4/2004 | Nawrocki et al. | |
| 2004/0077948 A1 | 4/2004 | Violante et al. | |
| 2004/0086542 A1 | 5/2004 | Hossainy et al. | |
| 2004/0172120 A1 | 9/2004 | Cheng et al. | |
| 2004/0258931 A1 | 12/2004 | Zamora et al. | |
| 2004/0260269 A1 | 12/2004 | Assaf | |
| 2004/0266302 A1 | 12/2004 | DiSalvo et al. | |
| 2005/0064088 A1 | 3/2005 | Fredrickson | |
| 2005/0158470 A1 | 7/2005 | Maiorino | |
| 2005/0226993 A1 | 10/2005 | Nawrocki et al. | |
| 2005/0240223 A1 | 10/2005 | Roby et al. | |
| 2005/0255249 A1 | 11/2005 | Schlatterbeck et al. | |
| 2006/0190040 A1 | 8/2006 | Roby | |
| 2006/0224237 A1 | 10/2006 | Furst et al. | |
| 2006/0257667 A1 | 11/2006 | Yokoyama et al. | |
| 2007/0024270 A1 | 2/2007 | Kawamura | |
| 2007/0128343 A1 | 6/2007 | Chappa | |
| 2007/0149629 A1 | 6/2007 | Donovan et al. | |
| 2007/0254091 A1 | 11/2007 | Fredrickson et al. | |
| 2007/0267464 A1 | 11/2007 | Vitcak et al. | |
| 2007/0299402 A1 | 12/2007 | Ishii et al. | |
| 2008/0071228 A1 | 3/2008 | Wu et al. | |
| 2008/0102192 A1 | 5/2008 | Johnson et al. | |
| 2008/0139683 A1 | 6/2008 | Flynn et al. | |
| 2008/0147117 A1 | 6/2008 | Cichocki et al. | |
| 2008/0277448 A1 | 11/2008 | Roby et al. | |
| 2009/0026291 A1 | 1/2009 | Shimada | |
| 2009/0148496 A1 | 6/2009 | Schmitz et al. | |
| 2011/0081486 A1 | 4/2011 | McCamy et al. | |
| 2011/0111116 A1 * | 5/2011 | Maurer | B05D 5/00 |
| | | | 427/2.28 |
| 2011/0112565 A1 | 5/2011 | Maurer et al. | |
| 2011/0112566 A1 | 5/2011 | Maurer et al. | |
| 2013/0189422 A1 | 7/2013 | Maurer et al. | |
| 2013/0209664 A1 | 8/2013 | Maurer et al. | |
| 2015/0367039 A1 * | 12/2015 | Ou | B05D 1/18 |
| | | | 427/2.28 |
| 2016/0157859 A1 | 6/2016 | Maurer et al. | |
| 2018/0235606 A1 | 8/2018 | Maurer et al. | |

FOREIGN PATENT DOCUMENTS

| | | |
|---|---|---|
| EP | 1048391 A2 | 11/2000 |
| EP | 2057946 A1 | 5/2009 |
| GB | 2292808 A | 3/1996 |
| JP | 2005306902 A | 11/2005 |
| WO | 9832474 A1 | 7/1998 |
| WO | 2007024270 A1 | 3/2007 |

OTHER PUBLICATIONS

[No Author Listed] 3M Material Safety Data Sheet for HFE-72DE. Nov. 16, 2007, 9 pages.

[No Author Listed] Momentive® Performance Materials Product Description for Product Code Nos. SS4004P, SS4044P, SS4120, SS4155, and SS4179. Retrieved from <http://www.momentive.com/momentiveInternetDoc/MPM/Static%20Files/Documents> on Apr. 27, 2010. 2003-2010, 4 pages.

[No Author Listed] Momentive® Performance Materials Safety Data Sheet for Product Code No. SS4044P. Version 1.6, Mar. 28, 2008, 9 pages.

[No Author Listed] NuSil® Technologies Material Safety Data Sheet for DSP-9769. Oct. 3, 1996, 7 pages.

[No Author Listed] NuSil® Technologies MED-4162 Product Profile. Dec. 2006, 2 pages.

[No Author Listed] Petroleum ether: dp 30-40° C., low boiling point hydrogen treated naphtha, puriss. p.a. Sigma Aldrich. SKU # 77399. 3 Pages, 2014. Rretrieved from <http://www.sigmaaldrich.com/catalog/product/sial/77399> on Feb. 19, 2014.

[No Author Listed] Sigma-Aldrich, Tetraethyl orthosilicate. Retrieved from <http://www.sigmaaldrich.com/catalog/product/aldrich/333859?> on Oct. 10, 2014, 3 pages.

[No Author Listed] Techsil, Momentive SS4044 Primer clear 500ml. Retrieved from <http://www.techsil.co.uk/applications/printing/momentive-ss40> on Oct. 10, 2014, 2 pages.

International Search Report and Written Opinion for Application No. PCT/US2010/53541, dated Dec. 28, 2010 (12 pages).

International Preliminary Report on Patentability for Application No. PCT/US2010/053541, dated May 24, 2012 (7 pages).

International Search Report and Written Opinion for Application No. PCT/US2010/53545, dated Jan. 3, 2011 (15 pages).

International Preliminary Report on Patentability for Application No. PCT/US2010/053545, dated May 24, 2012 (8 pages).

International Search Report and Written Opinion for Application No. PCT/US2010/53552, dated Dec. 21, 2010 (15 pages).

International Preliminary Report on Patentability for Application No. PCT/US2010/053552, dated May 24, 2012 (8 pages).

U.S. Appl. No. 12/614,669, filed Nov. 9, 2009, entitled "Surgical Needle Coating and Methods" (44 pages).

International Preliminary Report on Patentability issued in International Patent Application No. PCT/IB2018/056938, dated Mar. 26, 2020 (10 pages).

U.S. Appl. No. 12/614,665, filed Nov. 9, 2009, entitled "Surgical Needle Coating and Methods" (44 pages).

Govaerts et al. "Using Hydrofluoroether Solvents to Replace HCFC-141b, Part I", Medical Device Technology, (Oct. 2001) 12(8):31-34.

Tsai Wen-Tien "Environmental Risk Assessment of Hydrofluoroethers (HFEs).", Journal of Hazardous Materials, (Jan. 26, 2005) 119(1-3):69-78.

"Methods for Coating Surgical Suture Needles", Kenneth Publications, Hampshire, UK, GB 503(68):3 pages, Mar. 2006.

* cited by examiner

SURGICAL COATED NEEDLES

CROSS-REFERENCE TO RELATED APPLICATIONS

This application claims the benefit of U.S. Provisional Patent Application 62/559,267, entitled "Surgical Coated Needles," filed on Sep. 15, 2017, which is incorporated herein by reference in its entirety.

BACKGROUND OF THE INVENTION

Medical devices which repeatedly come into contact with bodily tissue, such as surgical needles, are required to be lubricious, yet durable enough to withstand multiple contacts with tissue. Suitable lubricity is often imparted to the medical devices by applying one or more coating compositions to the medical devices. For example, silicone based compositions.

Typically, surgical needles have a distal piercing point (tissue-penetrating tip) and a proximal suture mounting section (suture attachment end). The proximal suture mounting sections are typically a channel formed in the proximal end or a bore hole laser drilled into the proximal end. The lubricious coatings are applied to the surgical needles prior to being laser drilled. However, due to the energy required for laser drilling, the coatings can char during laser drilling. Charring can lead to gumming/fouling of the cutoff dies. Additionally, this charring can lead to visual defects and/or reduction in lubricity of the surgical needles.

Accordingly, there remains a need for improved surgical needles, systems, and methods that address current issues with laser drilling surgical needles.

BRIEF SUMMARY OF THE INVENTION

Systems and methods for coating surgical needles are provided herein.

In one embodiment, a system can include a first coating system, a laser drilling system, and a second coating system. The first coating system can be configured to apply at least one of a primer coat and a base coat to a first portion of a surgical needle blank. The laser drilling system can be configured to create a suture attachment end within a second portion of the surgical needle blank, thereby forming the surgical needle. The second coating system can be configured to apply a top coat to the surgical needle. The second coating system can include a basket that can be configured to house the surgical needle during application of the top coat. The basket can have a base portion, a top portion, and a first and a second pair of opposing sidewalls each extending from the base portion to the top portion, thereby defining a total surface area of the basket. The basket can have a drainage area that is from about 50% to 95% of the total surface area. In one aspect, the first coating system can be a spray coating system.

In some aspects, the system can include a first drying system that can be configured to remove at least a portion of excess top coat from the surgical needle. In one aspect, the drying system can include a vacuum drying chamber. In other aspects, the system can include a second drying system that can be configured to remove at least a portion of solvent from the top coat.

In some aspects, the system can include a curing system that can be configured to at least partially cure at least one of the primer coat and the base coat.

The basket can have a variety of configurations. For example, in some aspects, the base portion can include a porous substrate that can be configured to retain the surgical needle within the basket and allow at least a portion of excess top coat to pass therethrough. In such aspects, the top portion can include a porous substrate that is configured to allow air to pass therethrough. In such aspects, each sidewall can have an inner surface and an outer surface with one or more drainage holes extending therebetween, the one or more drainage holes can be configured to allow at least a portion of excess top coat to pass therethrough, and the one or more drainage holes can remain open when the top portion is in contact with the inner surfaces.

Methods for coating a surgical needle are also provided. In one exemplary embodiment, the method can include spray coating a primer coat onto a portion of a surface of a surgical needle blank formed from a tungsten-rhenium alloy, the portion of the surgical needle blank having a tissue-penetrating end, spray coating a base coat that differs from the primer coat onto the primed surface of the surgical needle blank, laser-drilling the surgical needle blank to create a suture attachment end opposite the tissue-penetrating end, thereby forming the surgical needle, and dip coating a top coat that differs from the base coat onto the base coat and the suture attachment end. In one aspect, the top coat can be formed from a composition comprising a silicone at a concentration from about 1% to 3% by weight of the composition.

In some aspects, the method can include vacuum drying the top coat. In one aspect, the method can include, after vacuum drying, removing at least a portion of solvent from the top coat at a temperature from about 90° C. to 130° C.

In other aspects, dip coating the top coat can include placing the surgical needle in a basket and placing the basket into a top coating solution, where the basket has a drainage area that is from 50% to about 95% of a total surface area of the basket. In such aspects, the basket can have a base portion, a top portion, and a first and a second pair of opposing sidewalls each extending from the base portion to the top portion, where the base and top portions can each include a porous substrate and the sidewalls can each include one or more drainage holes.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

This invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices, such as surgical needles, systems, and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Surgical needles and systems and methods for coating the same are provided. In general, a surgical needle is provided having an elongate body with a tissue penetrating end on a distal end thereof for penetrating through tissue. The tissue penetrating end can be pointed and can be as sharp or as dull as required for a particular surgical procedure. The surgical needle also includes a suture attachment end disposed on a proximal end of the elongate body for receiving and retaining suture. The surgical needle can have any geometry known in the art, including straight, taper point, taper cut, cutting edge, bayonet-shaped, curved, circular, etc. In addition, the surgical needle can have any cross-section including, but not limited to, round body, rectangular body, square body, ovular body, and I-beam. A person skilled in the art will appreciate the various combinations of shapes and cross-sections possible for a given needle. Further, the surgical needles described herein are merely intended to represent certain exemplary embodiments.

Figure 1:
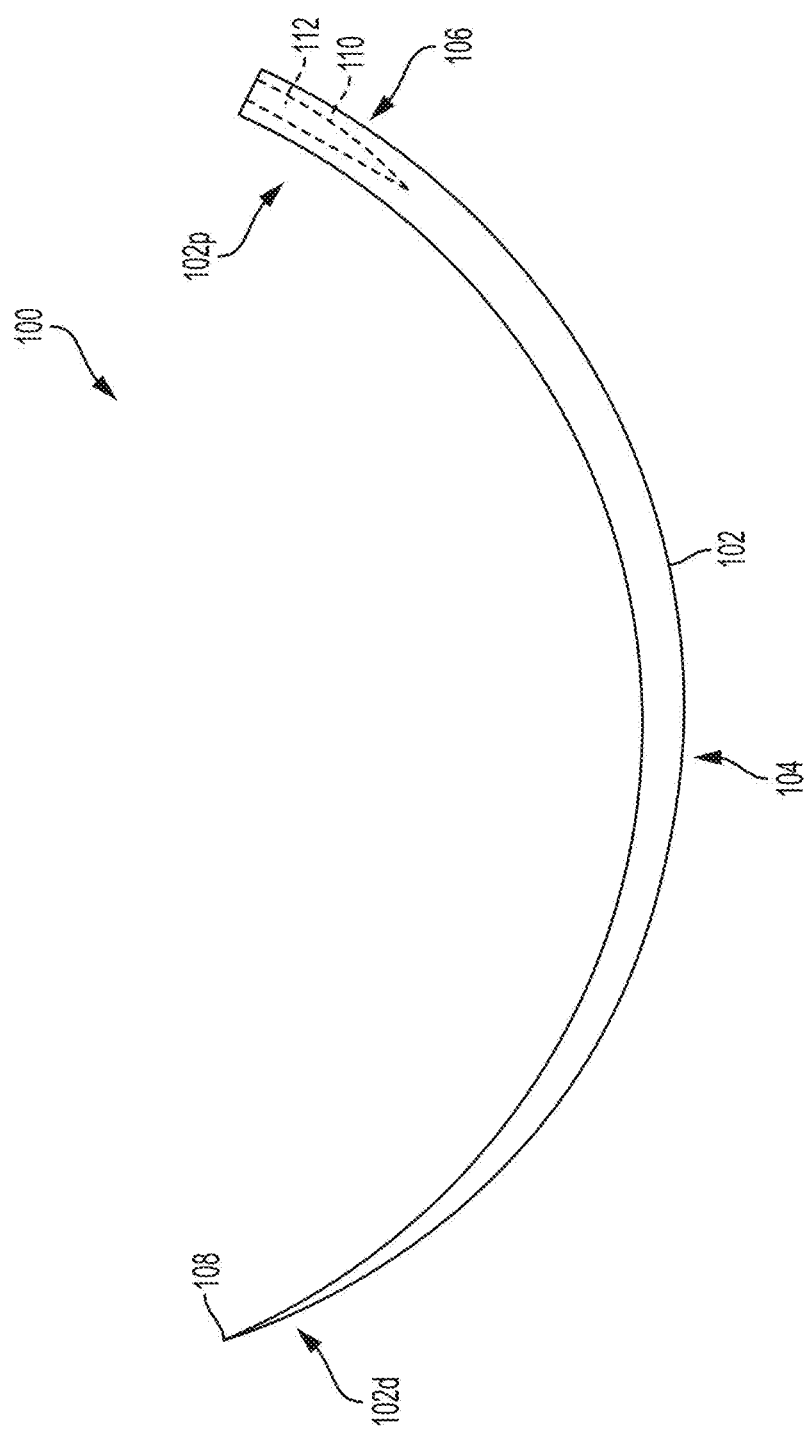
FIG. 1 is a side view of one exemplary embodiment of a surgical needle.
Figure 2:
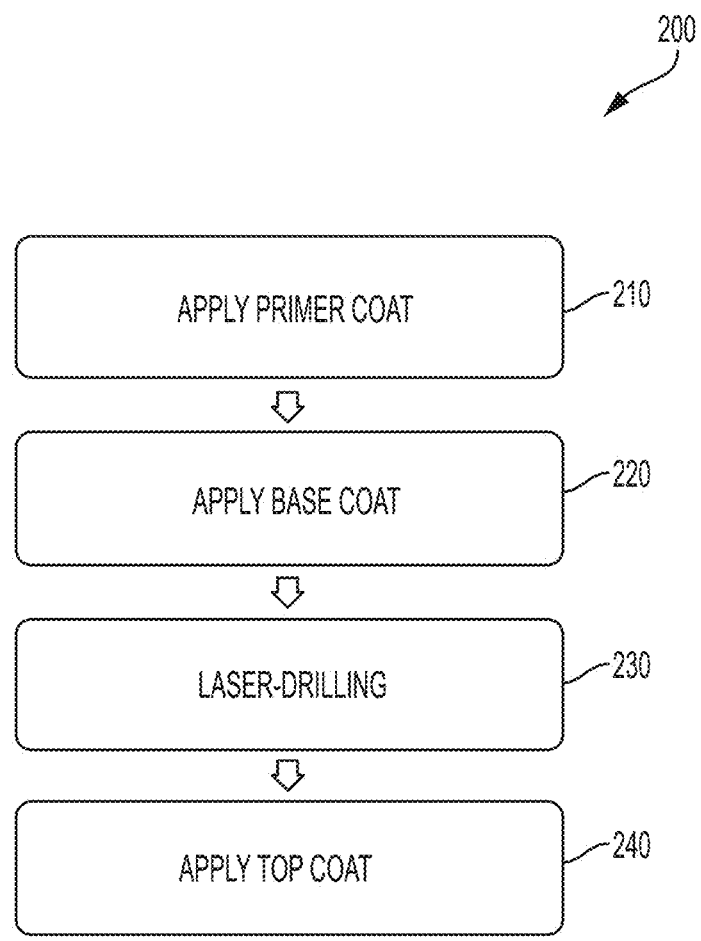
FIG. 2 is a flowchart of one exemplary method for coating surgical needles.
Figure 3A:
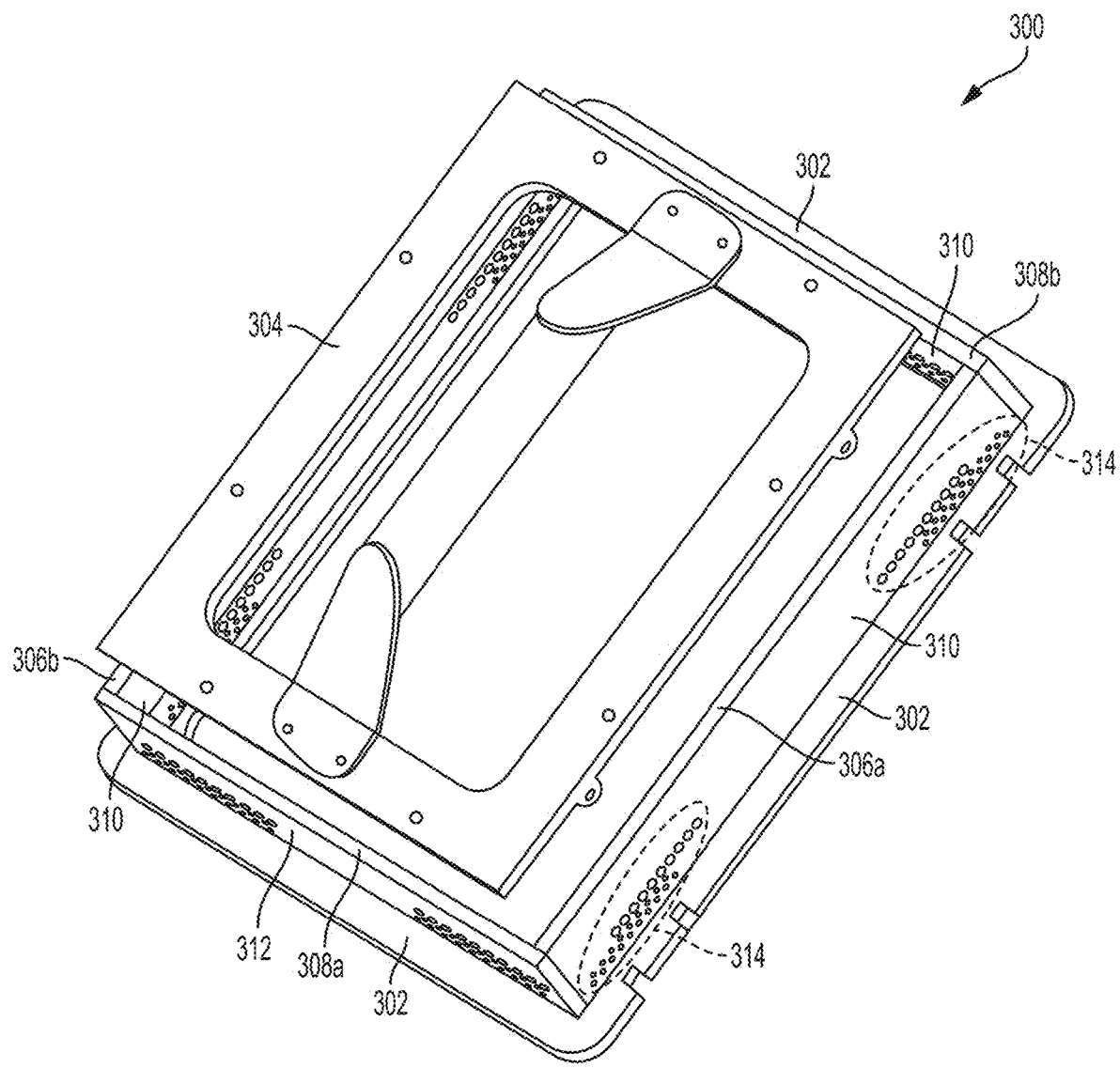
FIG. 3A is a top perspective view of one exemplary basket to be used in a dip coating process.
Figure 3C:
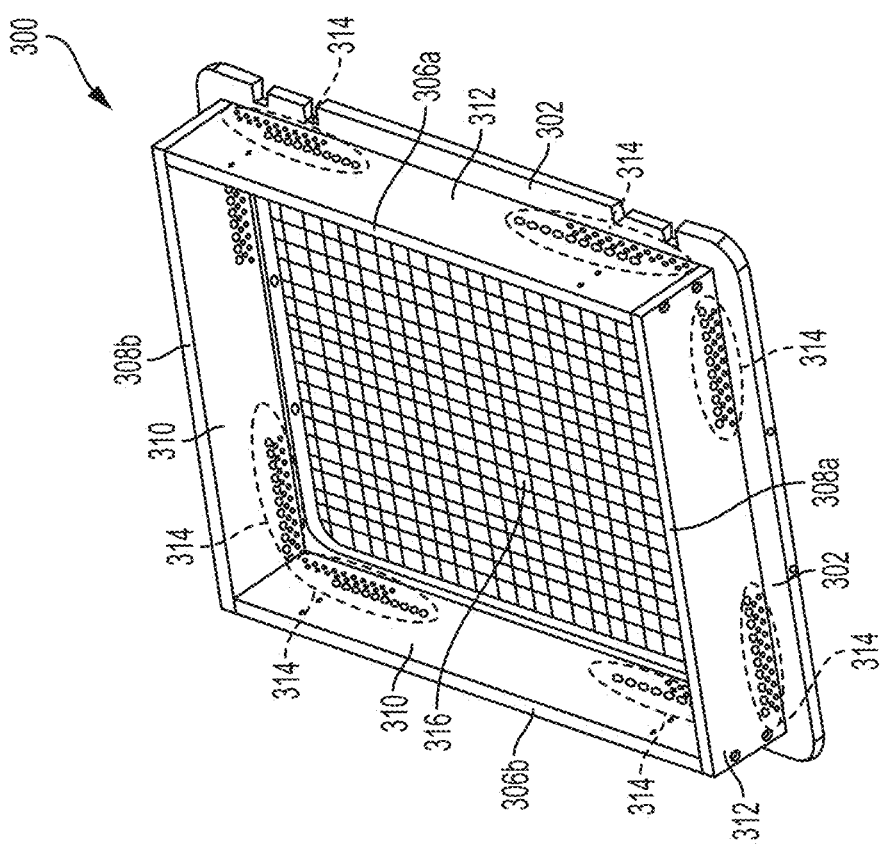
FIG. 3C is a top perspective view of the basket shown in FIG. 3A with the top portion removed.
Figure 3B:
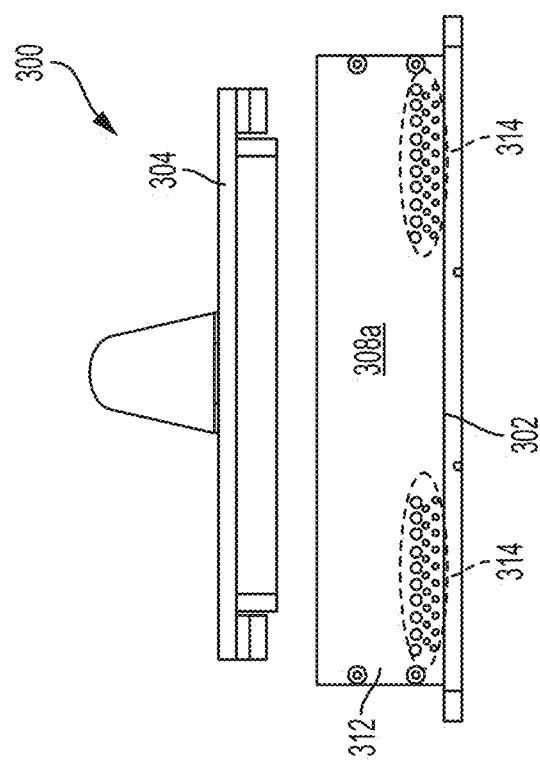
FIG. 3B is a side view of the basket shown in FIG. 3A.

FIG. 1 illustrates one embodiment of a surgical needle 100. As shown, the surgical needle 100 has an elongate body 102 having first and second portions 104, 106. The first portion 104 has a tissue-penetrating end 108, which is illustrated as a pointed tip, at the distal end 102d of the elongate body 102. The second portion 106 has a suture attachment end (barrel) 110 at the proximal end 102p of the elongate body 102. The suture attachment end 110, as shown, includes a drilled bore hole 112. As described in more detail below, the first portion 104 of the surgical needle 100 is coated with a primer coat, a base coat, and a top coat, and the second portion 106 of the surgical needle 100 is coated with the top coat.

Exemplary surgical needles can be formed of any suitable, biocompatible material known in the art. In some embodiments, a surgical needle can be made of a metallic alloy, including, but not limited to, titanium, stainless steels such as 420 stainless steel, 455 stainless steel, ETHALLOY® Needle Alloy, and 302 stainless steel, refractory alloys, nitinol, tantalum, as well as various other materials and alloys known in the art. In other embodiments, surgical needles can be made from a tungsten-rhenium alloy. Use of tungsten-rhenium alloy in making surgical needles can give the needles greater stiffness, strength, and ductility than the use of some other materials. Increased stiffness and strength properties allow the needle to be resistant to elastic deformation and to thus resist bending and springing when pushed through tough tissue, for example, calcified tissue. Increased ductility prevents the needle from breaking when bent or curved by a surgeon. Any of the needle alloy compositions can contain some percentage of any one or more of nickel, cobalt, chromium, molybdenum, tungsten, rhenium, niobium, etc.

While the surgical needles described herein can vary in length, in some embodiments, the surgical needle can have a length from about 3 mm to 110 mm. In other embodiments, the surgical needle can have a length from about 5 mm to 10 mm or from about 50 mm to 90 mm.

In some embodiments, the surgical needle has a drag force that is less than a comparative drag force of a comparative surgical needle. As used herein, "comparative drag force" is drag force of a comparative surgical needle that is determined under the same conditions as the drag force of the (coated) surgical needle. Further, as used herein "comparative surgical needle" is a tungsten-rhenium alloy surgical needle without having a coating on the suture attachment end (non-barrel coated surgical needle). In certain embodiments, the surgical needle can have a drag force from about 15 grams to 100 grams, from about 60 grams to 100 grams, or from about 20 grams to 40 grams.

In other embodiments, the surgical needle has a tissue-penetrating force that is less than a comparative tissue-penetrating force of a comparative surgical needle. As used herein, "comparative tissue-penetrating force" is the tissue-penetrating force of a comparative surgical needle that is determined under the same conditions as the tissue-penetrating force of the (coated) surgical needle. In certain embodiments, the surgical needle can be configured to have a substantially constant tissue-penetrating force after at least thirty passes of the tissue-penetrating end of the elongate body of the surgical needle through tissue. As used herein, "substantially constant" when used to describe tissue-penetrating force can be used to mean, for example, within 10% of a specific tissue-penetrating force value, within 5% of the force value, or within 2% of the force value.

Systems and Methods for Manufacture

Typically, in a conventional manufacturing process of a surgical needle, wire made from a desired material is drawn in a wire mill to a desired diameter. The wire is then cut in conventional wire cutting equipment to produce needle blanks having the desired length. While it is understood that a "needle blank" is a needle without a suture attachment end (barrel), for purposes of this disclosure, the first and second portions of the needle blank are understood to be the same first and second portions of the resulting surgical needle. The needle blanks can then go through a series of manufacturing process steps including, for example, shaping, grinding, polishing, cleaning, and drilling to produce a surgical needle.

To increase the lubricity of the surgical needles, the surgical needles can be partially or fully coated with one or more coatings during the manufacturing process. Unlike with conventional surgical needles, the suture attachment ends of the surgical needles described herein are created prior to coating the exterior surface of the needle with a final top coating. That is, while the first portion of the surgical needle can have one or more coatings, such as primer and base coats, the second portion of the surgical needle remains uncoated until the suture attachment end is formed, and once formed, the first and second portions of the surgical needle are then coated with the final top coating. This is believed to avoid charring of the coating(s) that would otherwise occur when creating the suture attachment ends in conventional surgical needles. As a result, the lubricity and aesthetic appearance of the surgical needle can be maintained.

In general, as noted above, the surgical needles as described herein have a first portion that is coated with at least a primer coat, a base coat, and a top coat, and a second portion that is coated with at least the top coat. The primer coat can covalently bond to the surgical needle to provide a substrate on which to apply other coatings. The base coat can be applied on top of the primer coat. As the top coat is applied over the base coat, the base coat can bond with the top coat to provide durability to the top coat. In essence, the bonding between the primer coat and the surgical needle anchors the other two coats to the needle surface. The bonding of the base coat to both the primer coat and the top coat anchors the top coat to the primer coat, and thus to the surgical needle surface, giving the top coat extended durability.

The coatings can generally be applied at any thickness as needed. The thickness of the individual coatings and the combined coatings should be sufficient to effectively provide the desired characteristics. For example, the primer coat can be applied to have a thickness in the range of about 0.01 μm to about 1 μm. The base coat and the top coat can be applied with a thickness in the range of about 1 μm to about 10 μm. In an exemplary embodiment, the top coat can have a thickness that is at least about 50% less than a thickness of the base coat. A person skilled in the art will appreciate that the thicknesses of the coatings can vary depending on a particular application.

While many methods for coating surgical needles are contemplated, a flow chart of an exemplary embodiment of one method is illustrated in FIG. 200. As shown, the method can generally include applying a primer coat 210, for example, onto a portion of a surface of a surgical needle blank in which the portion of the surgical needle blank has a tissue-penetrating end, applying a base coat 220, for example, onto the primed surface of the surgical needle blank, laser-drilling 230, for example, the surgical needle blank to create a suture attachment end opposite the tissue-penetrating end, thereby forming the surgical needle, and applying a top coat 240, for example, onto the base coat and the suture attachment end of the surgical needle. Thus, during manufacturing, the suture attachment end of the surgical needle can be created in an uncoated portion of the needle, and then subsequently coated with a final top coat.

Primer Coat

While the application of the primer coat is optional, in some embodiments it is desirable as the use of a primer coat can be advantageous. For example, a primer coat can be capable of chemically bonding to the needle surface to provide a bonding substrate for the lubricious silicone coatings to adhere to, resulting in increased durability of the base and top coatings. For example, in one embodiment, a primer coat can be applied to the first portion 104 of surgical needle 100 illustrated in FIG. 1, prior to applying the base coat. It is also contemplated that a primer coat can include a single layer of primer coat or multilayers of the same or different primer coats.

The primer coat can have any formulation capable of bonding to a surgical needle blank and capable of providing an appropriate substrate for applying a base coat. In one embodiment, the primer coat can be formed of, for example, polyalkylsiloxane and tetraethyl silicate. A polyalkylsiloxane and tetraethyl silicate primer coat can be formulated for coating difficult-to-bond substrates such as, for example, tungsten-rhenium alloys. In other embodiments, the primer coat can be formed of vinyl triethoxysilane or (3-Glycidyloxypropyl)triethoxysilane.

Base Coat

As described above, the base coat can be applied to the primed surface of the surgical needle, such as primed first portion 104 of surgical needle 100 illustrated in FIG. 1, prior to forming, by laser-drilling, the suture attachment end of the surgical needle. It is also contemplated that a base coat can include a single layer of base coat or multilayers of the same or different base coats.

The base coat can include, for example, a silicone based composition characterized as a vinyl functionalized organopolysiloxane. The base coat solution includes a vinyl functionalized organopolysiloxane, polymethylhydrogen siloxane fluid crosslinking agent, and optionally a catalyst such as a conventional metal catalyst such as platinum or tin. The organopolysiloxane base polymer can be, for example, Momentive® Product Code No. MSC2631 silicone manufactured by Momentive® Performance Materials of Waterford, N.Y. Further information on the MSC2631 composition is available from the manufacturer's MSDS.

The base coat can be prepared using any high vapor pressure, low boiling point solvent known in the art. In some embodiments, the solvent can be a hydrofluoroether ("FIFE") (e.g., HFE 72-DE solvent manufactured by 3M® of St. Paul, Minn.). The HFE solvent acts as a carrier for the silicone composition. It evaporates quickly from a composition under ambient conditions to limit migration of other substances in the composition and thus drastically reduces cure time of the composition. In addition, the HFE solvent leaves no residue after evaporation. It complies with health and safety regulations and is environmentally friendly. As will be appreciated by those skilled in the art, any suitable solvent can be used including, but not limited to, HFE, xylene, heptane, Isopar K (Exxon Mobil), napthalene, toluene, and hydrofluorocarbons.

Additionally, a catalyst and a crosslinker can be added to the base coat. For example, Momentive® Product Code No. SS8010 platinum catalyst ("catalyst") and Momentive® Product Code No. SS4300 crosslinker ("crosslinker"), both manufactured by Momentive® Performance Materials of Waterford, N.Y., can be added during the preparation of the base coat to act as a crosslinker and catalyst. As will be appreciated by those skilled in the art, any suitable catalysts and crosslinkers can be used including, but not limited to, other crosslinkers containing a silicon-hydrogen moiety. Other catalysts may include conventional metal catalysts such as tin.

Top Coat

As described above, the top coat can be applied after the suture attachment end is formed in the surgical needle, such as suture attachment end 110 of surgical needle 100 illustrated in FIG. 1. That is, after laser drilling, the top coat can be applied to the base coat and onto the suture attachment end of the surgical needle. It is also contemplated that a top coat can include a single layer of top coat or multilayers of the same or different top coats.

The top coat can include, for example, a silicone based composition. In one embodiment, the top coat can be formed of a compositing having a silicone at a concentration between about 1% to 3% by weight of the composition. In another embodiment, the top coat can be formed of a compositing having a silicone at a concentration that is less than about 3% by weight of the composition. In other embodiments, the top coat can be formed of a compositing having a silicone at a concentration between about 2% to 2.75% or between about 2.25% to 2.5% by weight of the composition.

In some embodiments, the composition can have a viscosity from about 1 cPs to 5 cPs measured at a temperature of 25° C. In one embodiment, the composition can have a viscosity from about 2 cPs to 5 cPs measured at a temperature of 25° C. In another embodiment, the composition can have a viscosity from about 2 cPs to 3 cPs or from about 3 cPs to 4 cPs measured at a temperature of 25° C.

In some embodiments, the top coat can include a silicone based composition characterized as a hydroxyl terminated polydimethylsiloxane. The hydroxyl terminated polydimethylsiloxane generally includes dimethyl siloxane-hydroxy terminated, methylhydrogen siloxane, and trace amounts of several other siloxanes. The hydroxyl terminated polydimethylsiloxane can be, for example, NuSil® Technologies Silicone Product No MED4162 manufactured by NuSil® Technologies of Carpentaria, Calif., or Dow Corning Product No. Syl-Off® 23 manufactured by Dow Corning Corporation of Midland, Mich., each of which is a dispersion that contains 30% solids silicone in a 70% xylene solvent carrier.

The top coat can be prepared using a solvent, for example, a heptane solvent or any other compatible volatile-solvent. In preparing an exemplary top coat, 2.5 wt. % of the top silicone polymer can be combined with 91.7 wt. % of heptane solvent. For example, for a 100 g top coat sample, 2.5 g of the top silicone polymer in the form of 8.3 grams of NuSil® MED4162 can be combined with 91.7 g of heptane solvent.

While the top coat can have vary in thickness, in some embodiments, the top coat can be a thickness from about 0.1 micrometers to 10 micrometers. In other embodiments, the top coat can have a thickness from about 0.1 micrometers to 3 micrometers, from about 0.7 micrometers to 2 micrometers, or from 0.2 micrometers to 0.6 micrometers.

Coating Processes

Any process known in the art can be used to coat various surgical needles with one or more of a primer coat, a base coat, and a top coat, including, but not limited to, dipping, spraying, wiping, brushing, total immersion, gravity feed, etc. For example, in one embodiment, the surgical needles described herein can be spray coated with primer and base coats and then dip coated with a top coat.

In some embodiments, the primer and/or base coats can be applied to a surgical needle by spraying using, for example, ultrasonic and/or gas conformal coating spray nozzle systems and/or swirl coating systems. Ultrasonic and gas spray nozzles transmit energy to a liquid in an amount sufficient to atomize the liquid and form a spray of droplets. The spray of droplets can be applied to a medical device using a swirl process in which the droplets are swirled around the medical device in order to coat the substrate. Application of a coating using the swirl process can ensure a more even distribution of the coating to a surgical device while preventing excess collection of the coating that may result in drips, undesired pooling, droplets, and/or unevenness. Spraying also allows for precise control and adjustment of coating thickness. A particular coating can be applied to leave only a thin film on a surface or it can be applied to provide different thicknesses.

Different types and sizes of spray nozzles can be used depending on the specific coating compositions and the desired attributes of the spray stream generated. Spray nozzles can be designed to operate at specific frequencies and/or air pressures as needed and the desired power level for operating the nozzles can depend on various factors including the size and design of the nozzle, the viscosity of the composition being used, the volatility of components in the composition being used, etc. Both ultrasonic and fluid spray nozzles are available commercially.

Additional details on spray coating are disclosed in U.S. Pat. No. 9,259,219, entitled "Surgical Needle Coatings and Methods," which is incorporated herein by reference in its entirety.

Figure 4B:
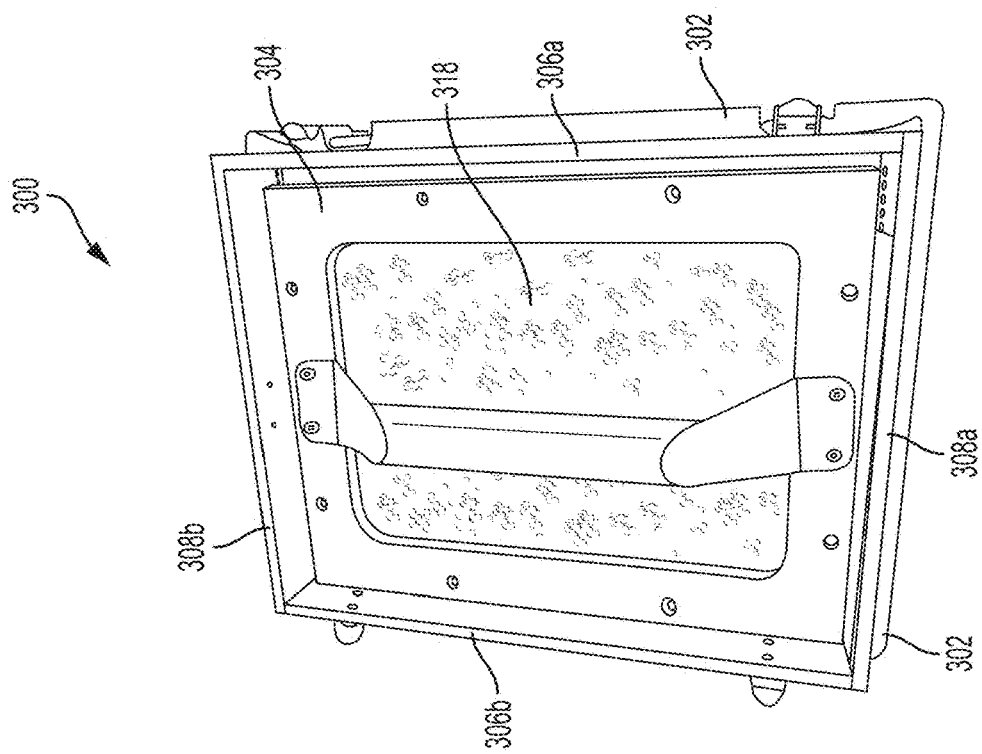
FIG. 4B is a top perspective view of the basket shown in FIG. 4A in a closed configuration (i.e., with the top portion in contact with the inner surfaces of the sidewalls.

In some embodiments, once bore hole is drilled into needle blank, thereby forming the surgical needle, the top coat can be applied to the surgical needle by dip coating. For example, the surgical needle can be placed in a basket, and the basket can then be dipped into a top coating solution. While the dip coating procedure is described with reference to a surgical needle, a person of skilled in the art will appreciate that numerous surgical needles could be placed into the basket, e.g., as shown in FIGS. 4A-4B, and a batch dip coating process can be performed, e.g., as described in the below Examples.

An exemplary embodiment of a basket 300 is illustrated in FIGS. 3A-4B. As shown, the basket 300 has a base portion 302, a top portion 304, and a first and a second pair of opposing side walls in which each sidewall 306a, 306b, 308a, 308b extends from the base portion 302 to the top portion 304. For purposes of simplicity, in FIGS. 3A and 3B, the basket 300 is not closed (i.e., the top portion 304 is not in contact with the sidewalls 306a, 306b, 308a, 308b), and in FIGS. 3C and 4A, the top portion 304 is not illustrated.

In one embodiment, the basket 300 can have a drainage area that is from about 50% to 95% of the total surface of the basket 300. As used herein, the "total surface area" of the basket is defined as the summation of the surface areas of the base portion, top portion, and sidewalls of the basket. As used herein, the "drainage area" of the basket is defined as the total area of the basket in which liquid can pass through. In another embodiment, the basket 300 can have a drainage area of at least about 65% of the total surface area of the basket 300. In other embodiments, the basket 300 can have a drainage area that is from about 50% to 75, from about 55% to 60% or from about 60% to 75% of the total surface of the basket 300.

Figure 4A:
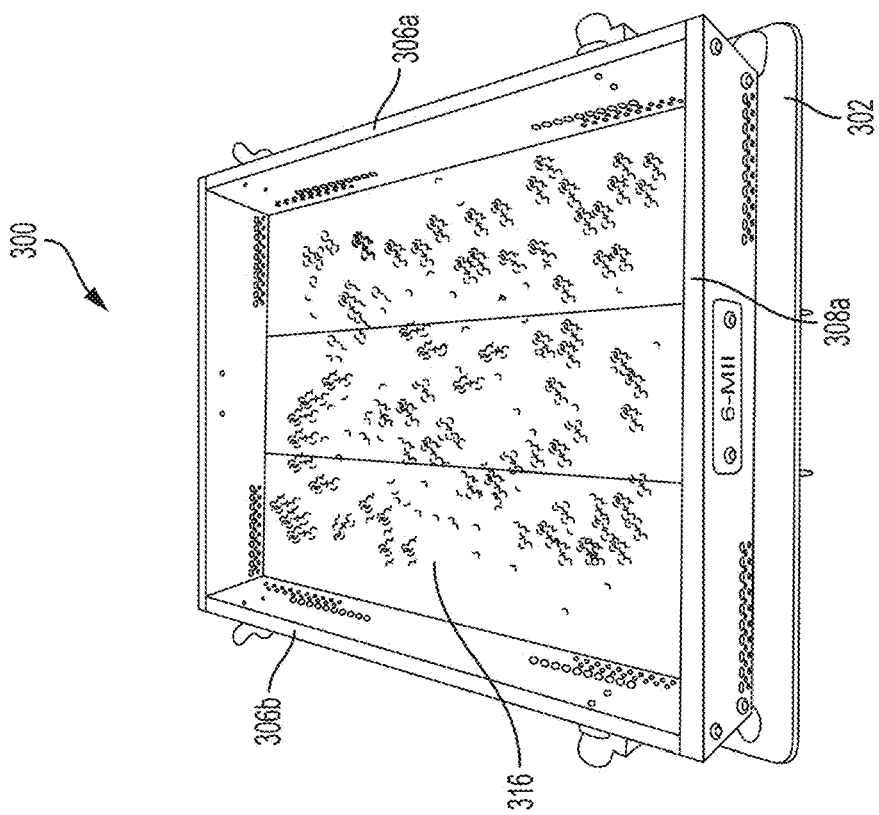
FIG. 4A is top perspective view of the basket shown in FIG. 3A with surgical needles disposed therein and with the top portion removed.

As shown in FIGS. 3A-4A, each sidewall 306a, 306b, 308a, 308b can include an inner surface 310 and an outer surface 312 with one or more drainage holes 314 extending therebetween. The one or more drainage holes 314 can allow liquid, such as the top coating composition, to pass through and out of the basket 300 during the dip coating process. Additionally, when the top portion 304 is placed in contact with the inner surfaces 310 of the sidewalls 306a, 306b, 308a, 308b so as to close the basket 300, as shown in FIG. 4B, the one or more drainage holes 314 remain open and therefore are not compromised when the basket 300 is closed. In one embodiment, as shown in FIGS. 3C-4B, the base portion 302 and the top portion 304 each include a porous substrate 316, 318. The porous substrate 318 of the base portion 302 can be configured to retain the surgical needle, illustrated as a curved needle in FIGS. 4A-4B, as shown in FIGS. 4A-4B, within the basket 300, while also allowing at least a portion of excess top coating to pass therethrough. The porous substrate 318 of the of the top portion 304 can be configured to allow air to pass therethrough, for example, during a vacuum drying process as described in more detail below. In addition, the porous substrate 318 of the top portion 304 can also prevent the surgical needle from floating within the basket 300, thereby preventing incomplete coating of the top coat onto the surgical needle. The design of the porous substrates 316, 318 are based at least in part on the size of the basket and the size of the surgical needle. For example, in one embodiment, the porous substrate 316 of the base portion 302 can be a 9.25"×11.5" mesh substrate and the porous substrate 318 of the top portion 304 can be 7"×9" mesh substrate, each having a mesh opening of 105 μm (e.g., SEFAR PROPYLTEX® 05-105/25).

Laser-Drilling

While needle blanks may be drilled in several ways, laser drilling is preferred. During this step, a suture attachment end is formed by drilling a bore hole into the uncoated proximal end of the needle blank, thereby forming the surgical needle. The laser systems typically use Nd:YAG lasers, but any laser type capable of providing the required power density and being focused to the required spot size is contemplated. Specific cycles are utilized to obtain the desired bore hole diameter and depth by controlling laser beam parameters including, but not limited to, beam power, energy density, energy density distribution, pulse shape, pulse duration, and the number of pulses. Exemplary laser-drilling processes and additionally details on such processes are described in U.S. Pat. No. 6,252,195, entitled "Method of forming blind holes in surgical needles using a diode pumped Nd-YAG laser," which is incorporated herein by reference in its entirety.

Figure 5:
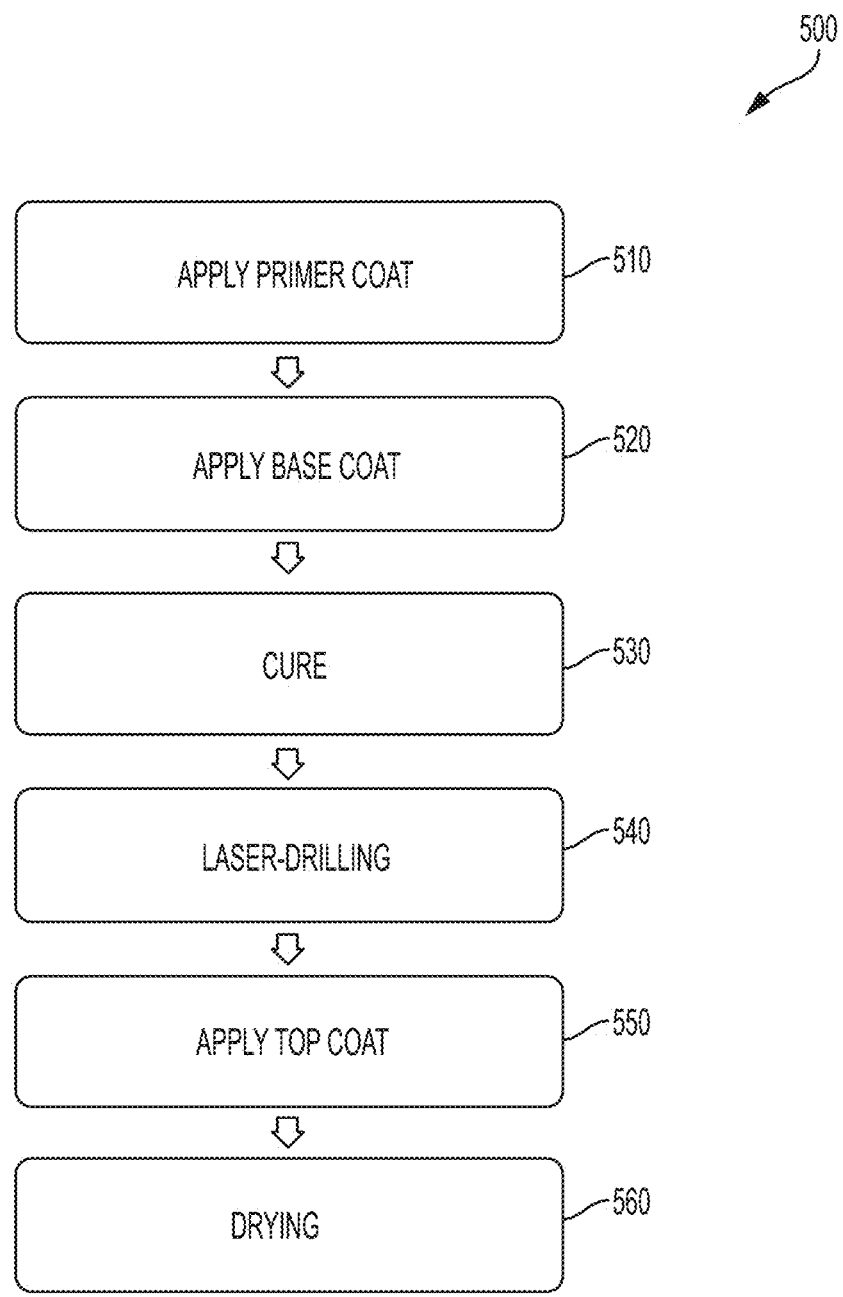
FIG. 5 is a flowchart of another exemplary method for coating surgical needles.

In some embodiments, as illustrated in FIG. 5, the method 500 can generally include applying a primer coat 510, for example, onto a portion of a surface of a surgical needle blank in which the portion of the surgical needle blank has a tissue-penetrating end, applying a base coat 520, for example, onto the primed surface of the surgical needle blank, curing the primer and base coats 530, laser-drilling 540, for example, the surgical needle blank to create a suture attachment end opposite the tissue-penetrating end, thereby forming the surgical needle, applying a top coat 550, for example, onto the base coat and the suture attachment end of the surgical needle, and drying the top coat 560. In some embodiments, the same curing system can be used to cure the primer and base coats, whereas in other embodiments, one curing system can be used to cure the primer coat and another curing system can be used to cure the base coat. It is contemplated that any of the coatings applied to the surgical needle can either be partially or completely cured or partially or completely dried. In one embodiment, the top coat is partially dried (i.e., a portion of solvent is removed from the top coat), and therefore partially crosslinked.

Figure 6:
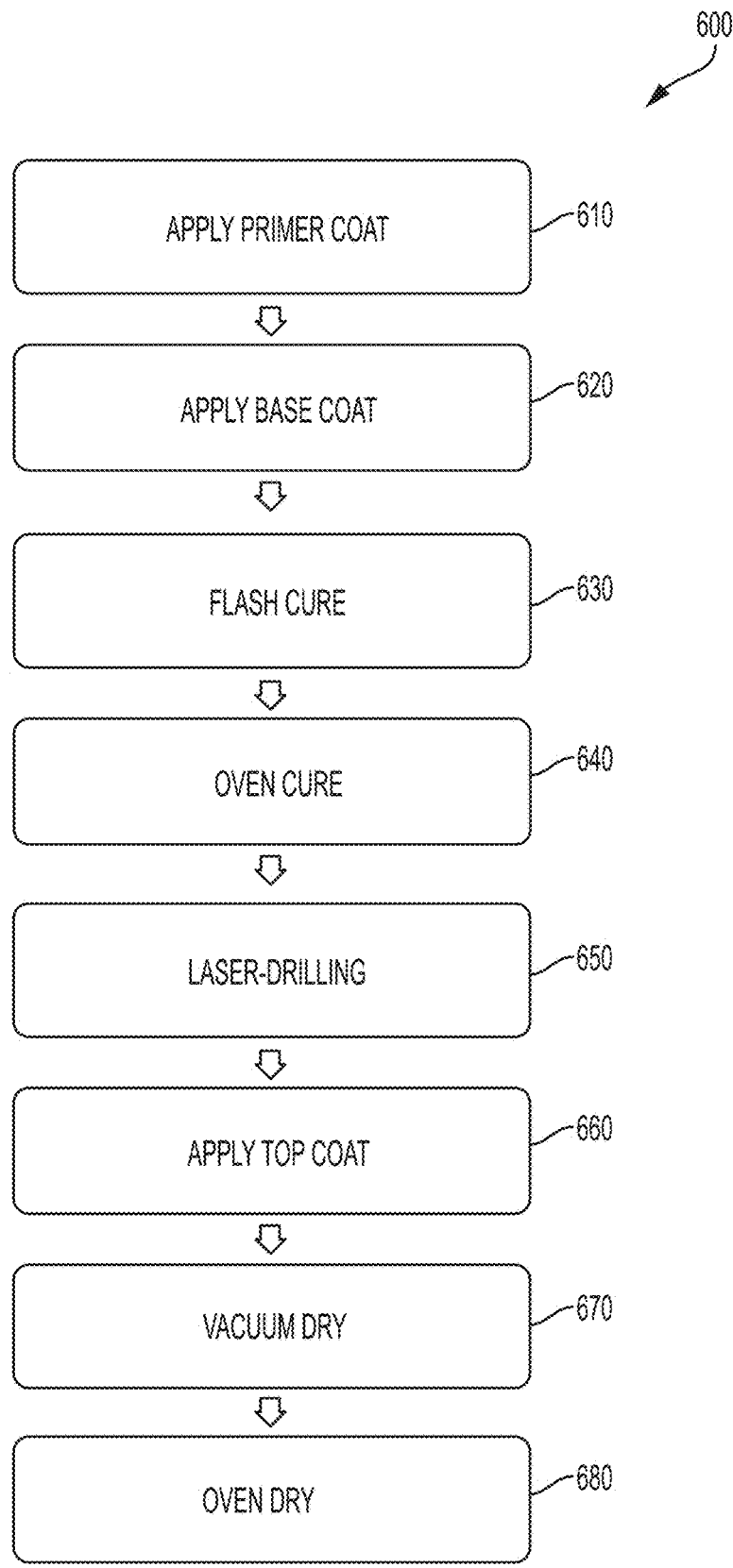
FIG. 6 is a flowchart of another exemplary method for coating surgical needles.

In other embodiments, as illustrated in FIG. 6, the method 600 can generally include applying a primer coat 610, for example, onto a portion of a surface of a surgical needle blank in which the portion of the surgical needle blank has a tissue-penetrating end, applying a base coat 620, for example, onto the primed surface of the surgical needle blank, flash curing the primer and base coats 630, oven curing the primer and base coats 640, laser-drilling 650, for example, the surgical needle blank to create a suture attachment end opposite the tissue-penetrating end, thereby forming the surgical needle, applying a top coat 660, for example, onto the base coat and the suture attachment end of the surgical needle, vacuum drying the top coat 670, and oven drying the top coat 680.

Curing Processes

There are many mechanisms known in the art for curing a coating on a surgical device such a surgical needle. Curing can also cause evaporation of any solvent used in making the coating. Curing can generally results in some type of chemical reaction and can be accomplished through exposure of a coated surgical needle to some form of temperature increase and/or humidity change for a predetermined period of time. For example, the coated needles can be placed in a furnace or oven, a hotbox, a humidification chamber, and/or an infrared chamber, among other forms known in the art. Curing times can range from "flash" curing of only a few seconds to times longer than twenty-four hours. In one embodiment, as shown in FIG. 6, the primer and base coats can be first flashed cured, followed by oven cured.

Exemplary curing processes and additionally details on such processes are described in U.S. Pat. No. 9,259,219, entitled "Surgical Needle Coatings and Methods," which is incorporated herein by reference in its entirety.

Drying Processes

Figure 7:
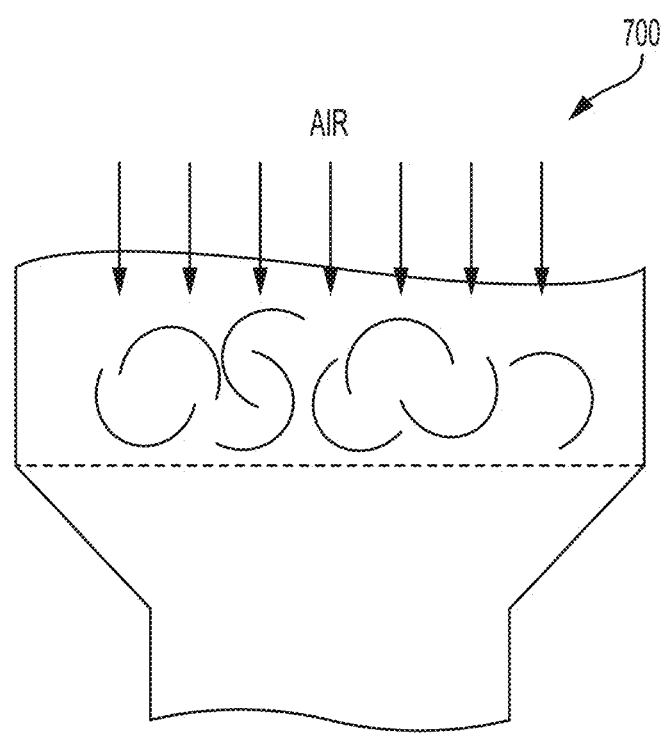
FIG. 7 is a side view of an exemplary vacuum drying chamber.

While any suitable drying process can be used to remove excess top coat, vacuum drying is preferred. In one embodiment, for example, once the surgical needle is dip coated with the top coat using a basket, such as basket 300 in FIGS. 3A-4B, the basket can be placed in a vacuum drying chamber, such as vacuum drying chamber 700 shown in FIG. 7. An exemplary vacuum drying process can include placing the basket 300, having surgical needle disposed therein, in a vacuum drying chamber and exposing the basket 300 to air flow (down draft) at about 1,400 ft/min for at least 15 minutes.

Further, there are many mechanisms that can be used for removing solvent, and therefore, setting a coating on a surgical device such a surgical needle. Setting a coating, unlike curing, generally does not result in a chemical reaction. Rather, setting a coating can include a suitable drying process that extracts solvent from the coating at a temperature that is less than the curing temperature of such coating. For example, in some embodiments, the top coat can be dried using an oven at a temperature from about 90° C. to 130° C. In other embodiments, the top coat can be oven dried at a temperature from about 90° C. to 110° C. or from about 110° C. to 120° C. In one embodiment, as shown in FIG. 6, a vacuum drying process can be used to remove excess top coat from the surgical needle, and an oven drying process can be used for solvent extraction from the top coat.

Systems

Various systems can be used to carry out the coating processes described herein. In general, the system can include one or more coating systems and a laser drilling system, in which the coating system(s) can be configured to apply at least one of the prime coat, the base coat, and the top coat, and the laser-drilling system can be configured to create a suture attachment end within the surgical needle blank, thereby forming the surgical needle. It is also contemplated that the system can include additional systems or units for carrying out the coating processes.

Figure 8:
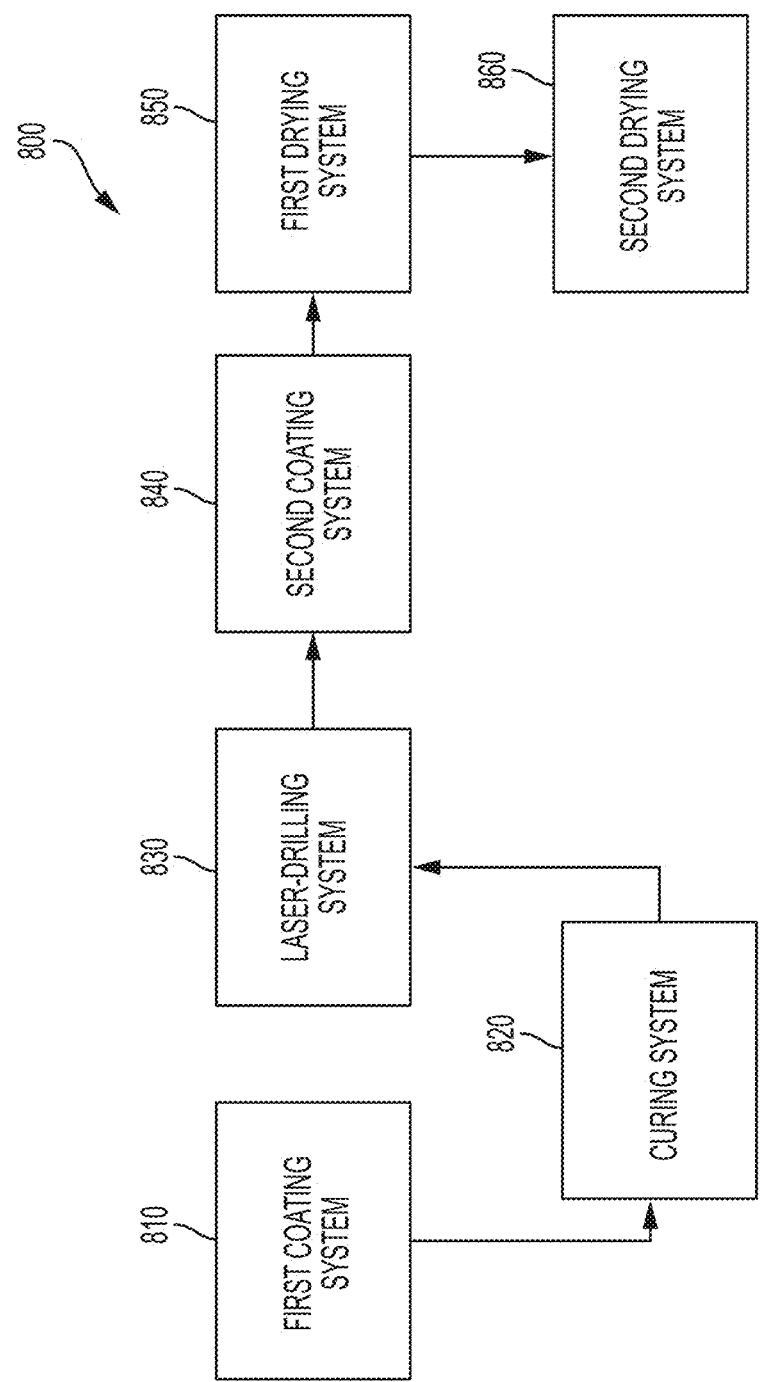
FIG. 8 is a process diagram of an exemplary system for coating surgical needles.

FIG. 8 illustrates one exemplary embodiment of a system 800 for coating a surgical needle, like surgical needle 100 in FIG. 1. As shown, the system 800 includes a first coating system 810, a curing system 820, a laser drilling system 830, a second coating system 840, and first and second drying systems 850, 860. The first coating system 810 can be configured to apply at least one of a primer coat and a base coat to a first portion of a surgical needle blank. In one embodiment, the first coating system 810 can be a spray coating system. The curing system 820 can be configured to at least partially cure the primer and base coats. The laser-drilling system 830 can be configured to create a suture attachment end within a second portion of the surgical needle blank, thereby forming a surgical needle. The second coating system 840 can be configured to apply a top coat to the surgical needle. In one embodiment, the second coating system 840 can be a dip coating process that uses a basket, such as basket 300 in FIGS. 3A-4B. As further shown in FIG. 8, the system 800 can include a first drying system 850 that can be configured to remove at least a portion of excess top coat from the surgical needle. In one embodiment, the drying system can include a vacuum drying chamber, like vacuum drying chamber 700 in FIG. 7. Further, the system 800 can include a second drying system 860 that can be configured to at least remove solvent from the top coat, thereby setting the top coat and producing the final coated surgical needle.

The surgical needles disclosed herein can be designed to be disposed of after a single use, or they can be designed to be used multiple times. In either case, however, the surgical needle can be reconditioned for reuse after at least one use. Reconditioning can include any combination of the steps of disconnecting the surgical needle from a suture material, followed by cleaning, and subsequent reconnection to the same or different suture material. Those skilled in the art will appreciate that reconditioning of a device can utilize a variety of techniques for disconnecting, cleaning, and reconnection. Use of such techniques, and the resulting reconditioned surgical needle, are all within the scope of the present application.

The present teachings may be further understood with reference to the following non-limiting examples.

EXAMPLES

The following experiments were conducted to examine the effect of coating the barrel of the surgical needles after the laser drilling process. Specifically, the effect on the lubricity of the resulting coated surgical needle. Additionally, the following experiments were conducted to examine the effect of silicone concentration and curing temperature of the top coating can have on the aesthetics and drag force of resulting surgical needles.

Protocol for Determination of Tissue-Penetration Force (Test B-ECNT Testing; ASTM No. F3014-4)

For each test sample, 30 needles were passed through Monmouth Duraflex MR40 NBR rubber membrane ("Monmouth rubber"), which serves to simulate flesh, or human cadaver tissue. The needles were individually passed through the penetration membrane thirty times each. The maximum force in grams was recorded for each pass and used as a measure of coating performance.

The surgical needles were mounted in a rotating stage to fix the needle in a position perpendicular to the penetration membrane surface and oriented on its radial profile with the axis of rotation on the same plane as the plane of the penetration membrane. The needle was rotated into the penetration membrane, which was mounted on top of the load cell. The maximum amount of vertical force was recorded as the needle was pushed through the penetration membrane.

Protocol for Determination of Drag Force

For each test sample, 30 needles were each passed through a test media (1/16 natural gum rubber sheet from Rubber-Cal). A Chatillon gauge was affixed to each needle tip, and each needle barrel was pulled through the test media at a speed of 10 in/minute. The maximum drag force in grams for each needle was recorded by the Chatillon gauge and the average was used a measure of maximum friction between the barrel of the needles and the test media.

Example 1A

Barrel-Coated Tungsten-Rhenium Needles: A lot of 6,000 10 mil BV-1 tungsten-rhenium BV-1 needles were prepared as follows:

Application of Primer Coat: A primer coating composition was prepared from a 1 to 1 (by weight) mixture of HFE and Momentive SS 4044P primer. A portion of the needles were swirl coated with the base coating composition using a single pass spray using the SC-300 Swirl Coat™ Applicator and the Century® C-341 Conformal Coating System available from Asymtek® of Carlsbad, Calif. with the following parameters: 2 PSI fluid pressure, 50 PSI air assist, and 10 in/sec line speed.

Application of First Base Coat: A first base coating composition was prepared from a mixture of 27.6 wt. % of Momentive MSC2631, 0.14% Momentive SS4300C and 0.025% Momentive SS8010, produced by Momentive Performance Material Inc., mixed with 72.2 wt. % of HFE-72DE solvent. The coated portion of the needles were swirl coated with the first base coating composition using a single pass spray using the SC-300 Swirl Coat™ Applicator and the Century® C-341 Conformal Coating System available from Asymtek® of Carlsbad, Calif. with the following parameters: 2 PSI fluid pressure, 50 PSI air assist, and 10 in/sec line speed.

Application of Second Base Coat: A second base coating composition was prepared using 26 wt. % of NuSil® MED4162 with 74 wt. % HFE-72DE solvent. The coated portion of the needles were swirl coated with the second base coating composition using a single pass spray with the following parameters: 10 PSI fluid pressure, 50 PSI air assist, and 5 in/sec line speed.

Curing: The coated needles were then flash cured in a heat tunnel for 30 seconds at 200° C., followed by oven cured for 10 hours at 190° C. The needles were then allowed to cool at ambient temperature outside the oven.

Laser-Drilling: The uncoated portion of the cooled needles (i.e., the proximal end) were each drilled to form bore holes using a conventional needle drilling Nd:Yag laser, thereby forming the suture attachment end (barrel) of the needles. The suture attachment ends were then water plugged in preparation of applying the top coat.

Application of Top Coat: The laser drilled needles were then placed into a dipping basket, as illustrated in FIGS. 4A-4B. The basket is formed of an aluminum frame having drainage holes in each side wall, and the base and top portions of the basket each include a polypropylene mesh (PROPYLTEX® Polypropylene manufactured by SEFAR, Specification: 05-105/25). The dipping basket was then dipped into a steel vessel having 5,000 mL of 2.5% Nusil® MED 4162 heptane solution.

Drying: The dipping basket was then placed into a vacuum drying chamber, such as the chamber 700 illustrated in FIG. 7, for 15 minutes. The needles were then transferred to an oven and dried at a temperature of 100° C. for 2 hours. The needles were then allowed to cool at ambient temperature outside the oven.

Non-Barrel-Coated Tungsten-Rhenium Needles (Control): A lot of 8,000 10 mil tungsten-rhenium BV-1 needles were prepared similar to the barrel-coated needles above, except that the suture attachment end (barrel) of the needles were not coated.

Barrel-Coated Steel Needles: A lot of 14,000 10 mil steel BV-1 needles were prepared as follows:

Application of Base Coat: The entire lot of needles were fixed on a steel strip and dipped into a solution consisting of 20% Nusil® MED4162 and 80% of Exxon Mobil Isopar™ K. The needles were then flash cured at 190° C. for 45 seconds.

Application of Top Coat: The flashed cured needles were then fixed on a steel strip and dipped into a solution consisting of 20% Nusil® MED4162 and 80% of Exxon Mobil Isopar™ K. The needles were then flash cured at 190° C. for 45 seconds.

Laser-Drilling: The proximal end of the coated needles were then each drilled to form bore holes using a conventional needle drilling Nd:Yag laser, thereby forming the suture attachment end (barrel) of the needles, and consequently, the barrel-coated steel needles.

Testing

Test A: Visual testing was performed on the barrel-coated tungsten-rhenium needles in which 1,000 needles were visually scanned, using the human eye, for silicone related defects. No silicone related defects were identified.

Test B: ECNT testing was performed on the barrel-coated tungsten-rhenium BV-1 needles (Test B1) and the non-barrel coated tungsten-rhenium BV-1 needles (Test B2). 30 needles from each batch were individually passed through the media 30 times each. The maximum force was recorded for each pass and used as a measure of the coating performance. The results are illustrated in FIG. 9.

Figure 9:
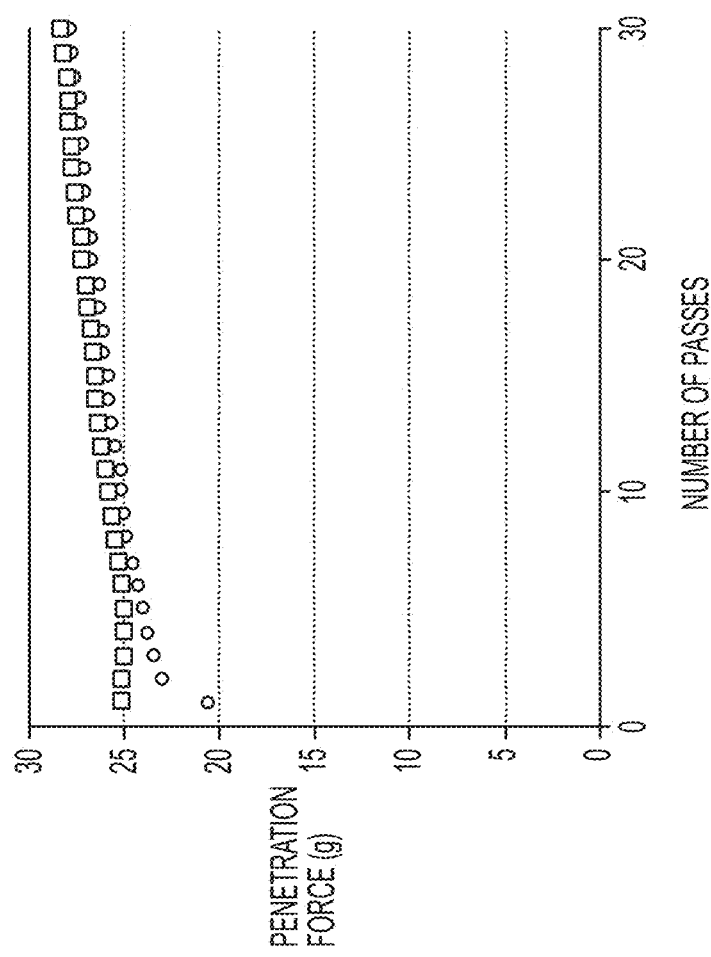
FIG. 9 is a graphical representation comparing the tissue-penetrating forces of barrel-coated tungsten-rhenium needles to non-barrel coated tungsten rhenium needles of Example 1A.

FIG. 9 is a graphical representation of the average results of Tests B1 and B2 in direct comparison. The y-axis shows the average penetration force in grams needed to pass the needles through the penetration membrane for each pass. The x-axis shows the number of passes. The diamonds represents the barrel-coated tungsten-rhenium BV-1 needles (Test B1) and the squares represent the non-barrel coated tungsten-rhenium BV-1 needles (Test B2). As can be seen, the barrel-coated tungsten-rhenium BV-1 needles had a first pass penetration performance of about 21 grams. In contrast, the non-barrel coated tungsten-rhenium BV-1 needles had a first pass penetration performance of about 26 grams. Thus, the barrel-coated tungsten-rhenium BV-1 needles had a more desirable first pass penetration performance compared to the non-barrel coated tungsten-rhenium BV-1 needles.

Test C: Barrel drag force testing was performed on the barrel-coated tungsten-rhenium BV-1 needles (Test C1), the non-barrel coated tungsten-rhenium BV-1 needles (Test C2), and barrel-coated steel BV-1 needles (Test C3). For each test, the barrels of the 30 needles are individually passed through the media. The maximum force is recorded during the pass using a Chatillon gauge and used as a measure of the barrel drag performance. The results are illustrated in Table 1 below.

TABLE 1

Measured Drag Force Results

| Sample | Maximum Drag Force (g) |
|---|---|
| Barrel-Coated Tungsten-Rhenium BV-1 Needles | 52 |
| Non-Barrel Coated Tungsten-Rhenium BV-1 Needles (Control) | 93 |
| Barrel-Coated Steel BV-1 Needles | 42 |

As can be seen in table 1, the maximum barrel drag force of the barrel-coated tungsten-rhenium BV-1 needles (Test C1) was found to be lower than the maximum barrel drag force of the control non-barrel coated tungsten-rhenium BV-1 needles (Test C2). Further, the maximum barrel drag performance of the barrel-coated tungsten-rhenium BV-1 needles (Test C1) was found to be comparable to the maximum barrel drag force of the barrel-coated steel BV-1 needles (Test C3).

Comparative Example 1A

Barrel-Coated Tungsten-Rhenium Needles: A lot of 2,000 8 mil tungsten-rhenium BV175-8 needles were prepared similar to barrel-coated tungsten-rhenium needles in Example 1A, except that the top coating composition was a 3% Nusil® MED 4162 heptane solution, and the fully coated needles were cured at 190° C. for 8 hours.

Non-Barrel-Coated Tungsten-Rhenium Needles (Control): A lot of 8,000 8 mil BV175-8 tungsten-rhenium needles were prepared in the same manner as the non-barrel-coated needles in Example 1A.

Barrel-Coated Steel Needles: A lot of 8,000 8 mil steal BV175-8 needles were prepared in the same manner as the barrel-coated steel needles in Example 1A.

Testing

Figure 10:
FIG. 10 is an image of a portion of the barrel-coated tungsten-rhenium needles of Comparative Example 1A.

Test A: Visual testing was performed on the barrel-coated tungsten-rhenium needles in which 300 needles were visually scanned, using the human eye, for silicone related defects. Thirty-eight needles with silicone related defects were identified. For example, FIG. 10 is an image of a portion of the thirty-eight needles with silicone related defects.

Test C: Barrel drag force testing was performed on the barrel-coated tungsten-rhenium BV175-8 needles (Test C1), the non-barrel coated tungsten-rhenium BV175-8 needles (Test C2), and barrel-coated steel BV175-8 needles (Test C3). For each test, the barrels of the 30 needles are individually passed through the media. The maximum force is recorded during the pass using a Chatillon gauge and used as a measure of the barrel drag performance. The results are illustrated in Table 2 below.

TABLE 2

Measured Drag Force Results

| Sample | Maximum Drag Force (g) |
|---|---|
| Barrel-Coated Tungsten-rhenium BV175-8 Needles | 30 |
| Non-Barrel Coated Tungsten-rhenium BV175-8 Needles (Control) | 78 |
| Barrel-Coated Steel BV175-8 Needles | 32 |

As can be seen in Table 2, the maximum barrel drag force of the barrel-coated tungsten-rhenium BV175-8 needles (Test C1) was found to be lower than the maximum barrel drag force of the control non-barrel coated tungsten-rhenium BV175-8 needles (Test C2). Further, the maximum barrel drag performance of the barrel-coated tungsten-rhenium BV175-8 needles (Test C1) was found to be lower than the maximum barrel drag force of the barrel-coated steel BV175-8 needles (Test C3).

Example 1B

Barrel-Coated Tungsten-Rhenium Needles (Post-Laser Drilling): A lot of 6,000 8 mil tungsten-rhenium BV175-8 needles were prepared in the same manner as the barrel-coated tungsten-rhenium needles in Example 1A.

Non-Barrel-Coated Tungsten-Rhenium Needles (Control): A lot of 8,000 8 mil tungsten-rhenium BV175-8 needles were prepared in the same manner as the non-barrel-coated needles in Example 1A.

Barrel-Coated Steel Needles: A lot of 8,000 8 mil steel BV175-8 needles were prepared in the same manner as the barrel-coated steel needles in Example 1A.

Testing

Test A: Two rounds of visual testing were performed on the barrel-coated tungsten-rhenium needles. In the first round 1,000 needles were visually scanned, using the human eye, for silicone related defects. Four needles were determined to have silicone related defects. In the second round, 300 needles were visually scanned, using the human eye, for silicone related defects. No silicone related defects were identified.

Test B: ECNT testing was performed on the barrel-coated tungsten-rhenium BV-1 needles (Test B1) and the non-barrel coated tungsten-rhenium BV-1 needles (Test B2). 30 needles from each batch were individually passed through the media 30 times each. The maximum force was recorded for each pass and used as a measure of the coating performance. The results are illustrated in FIG. 9.

Figure 11:
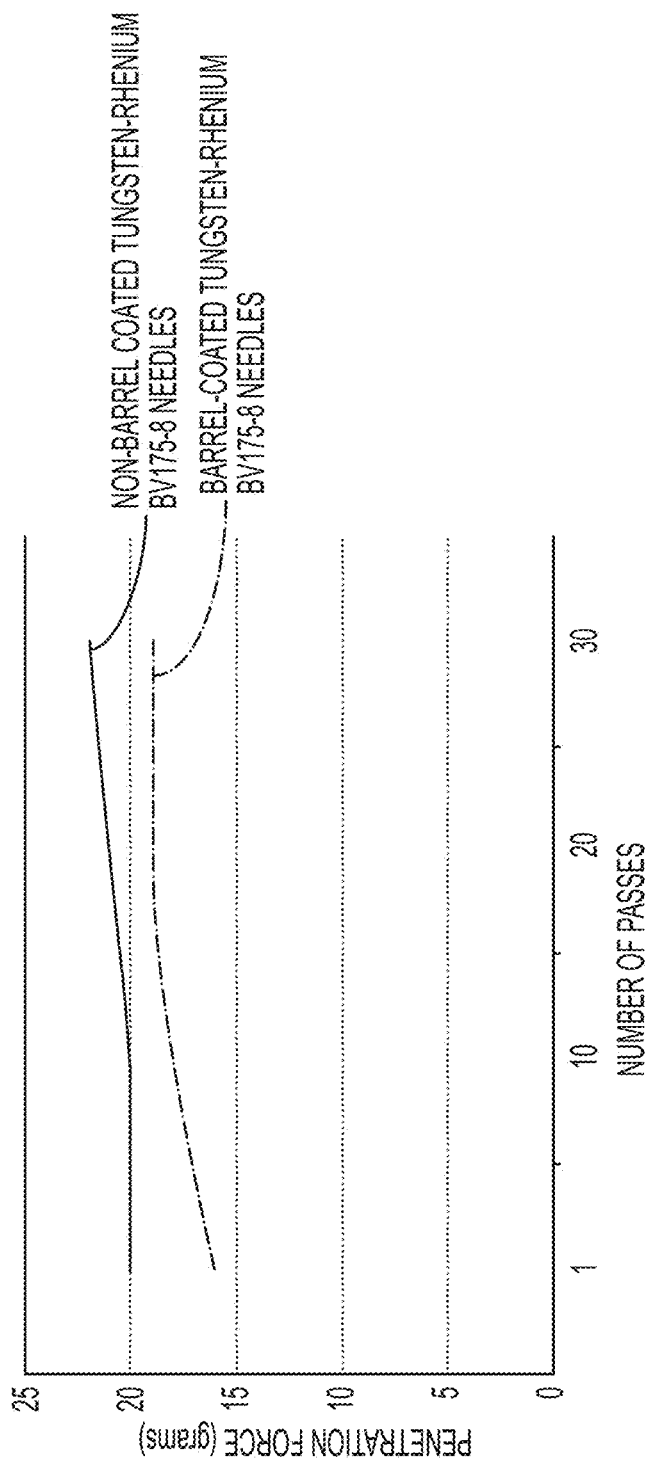
FIG. 11 is a graphical representation comparing the tissue-penetrating forces of barrel-coated tungsten-rhenium needles to non-barrel coated tungsten rhenium needles of Example 1B.

FIG. 11 is a graphical representation of the average results of Tests B1 and B2 in direct comparison. The y-axis shows the average penetration force in grams needed to pass the needles through the penetration membrane. For each pass the x-axis shows the number of passes. As can be seen, the barrel-coated tungsten-rhenium BV-1 needles had a first pass penetration performance of about 16 grams. In contrast, the non-barrel coated tungsten-rhenium BV-1 needles had a first pass penetration performance of about 20 grams. While the penetration force of the barrel-coated tungsten-rhenium BV-1 needles steadily increased over the thirty passes, for each pass the average penetration force of the barrel-coated tungsten-rhenium BV-1 needles was desirably less than the average penetration force of the non-barrel coated tungsten-rhenium BV-1 needles. Ultimately, the barrel-coated tungsten-rhenium BV-1 needles required about 4 grams less maximum force after thirty passes than the non-barrel coated tungsten-rhenium BV-1 needles.

Test C: Barrel drag force testing was performed on the barrel-coated tungsten-rhenium BV175-8 needles (Test C1), the non-barrel coated tungsten-rhenium BV175-8 needles (Test C2), and barrel-coated steel BV175-8 needles (Test C3). For each test, the barrels of the 30 needles are individually passed through the media. The maximum force is recorded during the pass using a Chatillon gauge and used as a measure of the barrel drag performance. The results are illustrated in Table 3 below.

TABLE 3

Measured Drag Force Results

| Sample | Maximum Drag Force (g) |
|---|---|
| Barrel-Coated Tungsten-rhenium BV175-8 Needles | 34 |
| Non-Barrel Coated Tungsten-rhenium BV175-8 Needles (Control) | 78 |
| Barrel-Coated Steel BV175-8 Needles | 32 |

As can be seen in table 3, the maximum barrel drag force of the barrel-coated tungsten-rhenium BV175-8 needles (Test C1) was found to be lower than the maximum barrel drag force of the control non-barrel coated tungsten-rhenium BV175-8 needles (Test C2). Further, the maximum barrel drag performance of the barrel-coated tungsten-rhenium BV175-8 needles (Test C1) was found to be comparable to the maximum barrel drag force of the barrel-coated steel BV175-8 needles (Test C3).

Comparative Example 1B

Barrel-Coated Tungsten-Rhenium Needles: A lot of 2,000 8 mil tungsten-rhenium BV175-8 needles were prepared similar to barrel-coated tungsten-rhenium needles in Example 1A, except that the top coating composition was a 3% Nusil® MED 4162 heptane solution, and the fully coated needles were cured at 100° C. for 2 hours.

Non-Barrel-Coated Tungsten-Rhenium Needles (Control): A lot of 8,000 8 mil tungsten-rhenium BV175-8 needles were prepared in the same manner as the non-barrel-coated needles in Example 1A.

Barrel-Coated Steel Needles: A lot of 8,000 8 mil BV175-8 steel needles were prepared in the same manner as the barrel-coated steel needles in Example 1A.

Testing

Test A: Visual testing was performed on the barrel-coated tungsten-rhenium needles in which 300 needles were visually scanned, using the human eye, for silicone related defects. Eight needles were determined to have silicone related defect(s).

Test C: Barrel drag force testing was performed on the barrel-coated tungsten-rhenium BV175-8 needles (Test C1), the non-barrel coated tungsten-rhenium BV175-8 needles (Test C2), and barrel-coated steel BV175-8 needles (Test C3). For each test, the barrels of the 30 needles are individually passed through the media. The maximum force is recorded during the pass using a Chatillon gauge and used as a measure of the barrel drag performance. The results are illustrated in Table 4 below.

TABLE 4

Measured Drag Force Results

| Sample | Maximum Drag Force (g) |
|---|---|
| Barrel-Coated Tungsten-rhenium BV175-8 Needles | 35 |
| Non-Barrel Coated Tungsten-rhenium BV175-8 Needles (Control) | 78 |
| Barrel-Coated Steel BV175-8 Needles | 32 |

As can be seen table 4, the maximum barrel drag force of the barrel-coated tungsten-rhenium BV175-8 needles (Test C1) was found to be lower than the maximum barrel drag force of the control non-barrel coated tungsten-rhenium BV175-8 needles (Test C2). Further, the maximum barrel drag performance of the barrel-coated tungsten-rhenium BV175-8 needles (Test C1) was found to be comparable to the maximum barrel drag force of the barrel-coated steel BV175-8 needles (Test C3).

Example 2

Barrel-Coated Tungsten-Rhenium Needles: A lot of 2,000 8 mil tungsten-rhenium BV175-8 needles were prepared similar to barrel-coated tungsten-rhenium needles in Example 1A, except that the top coating composition was a 2.25% Nusil® MED 4162 heptane solution, and the fully coated needles were cured at 90° C. for 75 minutes.

Non-Barrel-Coated Tungsten-Rhenium Needles (Control): A lot of 8,000 8 mil tungsten-rhenium BV175-8 needles were prepared in the same manner as the non-barrel-coated needles in Example 1A.

Barrel-Coated Steel Needles: A lot of 8,000 8 mil steel BV175-8 needles were prepared in the same manner as the barrel-coated steel needles in Example 1A.

Testing

Test A: Visual testing was performed on the Barrel-Coated Tungsten-Rhenium needles in which 300 needles were visually scanned, using the human eye, for silicone related defects. No visual silicone related defects were identified.

Test C: Barrel drag force testing was performed on the barrel-coated tungsten-rhenium BV175-8 needles (Test C1), the non-barrel coated tungsten-rhenium BV175-8 needles (Test C2), and barrel-coated steel BV175-8 needles (Test C3). For each test, the barrels of the 30 needles are individually passed through the media. The maximum force is recorded during the pass using a Chatillon gauge and used as a measure of the barrel drag performance. The results are illustrated in Table 5 below.

TABLE 5

Measured Drag Force Results

| Sample | Maximum Drag Force (g) |
| --- | --- |
| Barrel-Coated Tungsten-rhenium BV175-8 Needles | 39 |
| Non-Barrel Coated Tungsten-rhenium BV175-8 Needles (Control) | 78 |
| Barrel-Coated Steel BV175-8 Needles | 32 |

As can be seen in table 5, the maximum barrel drag force of the barrel-coated tungsten-rhenium BV175-8 needles (Test C1) was found to be lower than the maximum barrel draft force of the non-barrel coated tungsten-rhenium BV175-8 needles (Test C2). Further, the maximum barrel drag performance of the barrel-coated tungsten-rhenium BV175-8 needles (Test C1) was found to be comparable to the maximum barrel drag force of the barrel-coated steel BV175-8 needles (Test C3).

Comparative Example 2A

Barrel-Coated Tungsten-Rhenium Needles: A lot of 2,000 8 mil tungsten-rhenium BV175-8 needles were prepared similar to barrel-coated tungsten-rhenium needles in Example 1A, except that the top coating composition was a 1.5% Nusil® MED 4162 heptane solution, and the fully coated needles were cured at 100° C. for 2 hours.

Non-Barrel-Coated Tungsten-Rhenium Needles (Control): A lot of 8,000 8 mil tungsten-rhenium BV175-8 needles were prepared in the same manner as the non-barrel-coated needles in Example 1A.

Barrel-Coated Steel Needles: A lot of 8,000 8 mil steel BV175-8 needles were prepared in the same manner as the barrel-coated steel needles in Example 1A.

Testing

Test A: Visual testing was performed on the barrel-coated tungsten-rhenium needles in which 300 needles were visually scanned, using the human eye, for silicone related defects. Two needles were determined to have silicone related defect(s).

Test C: Barrel drag force testing was performed on the barrel-coated tungsten-rhenium BV175-8 needles (Test C1), the non-barrel coated tungsten-rhenium BV175-8 needles (Test C2), and barrel-coated steel BV175-8 needles (Test C3). For each test, the barrels of the 30 needles are individually passed through the media. The maximum force is recorded during the pass using a Chatillon gauge and used as a measure of the barrel drag performance. The results are illustrated in Table 6 below.

TABLE 6

Measured Drag Force Results

| Sample | Maximum Drag Force (g) |
| --- | --- |
| Barrel-Coated Tungsten-rhenium BV175-8 Needles | 67 |
| Non-Barrel Coated Tungsten-rhenium BV175-8 Needles (Control) | 78 |
| Barrel-Coated Steel BV175-8 Needles | 32 |

As can be seen in table 6, the maximum barrel drag force of the barrel-coated tungsten-rhenium BV175-8 needles (Test C1) was found to be lower compared to maximum barrel drag force of the control non-barrel coated tungsten-rhenium BV175-8 needles (Test C2). Further, the maximum barrel drag performance of the barrel-coated tungsten-rhenium BV175-8 needles (Test C1) was found to be higher than the maximum barrel drag force of the barrel-coated steel BV175-8 needles (Test C3).

Example 3

Barrel-Coated Tungsten-Rhenium Needles: A lot of 3,100 8 mil tungsten-rhenium BV175-8 needles were prepared similar to barrel-coated tungsten-rhenium needles in Example 1A, except that the top coating composition was a 2.75% Nusil® MED 4162 heptane solution, and the fully coated needles were cured at 110° C. for 3 hours.

Non-Barrel-Coated Tungsten-Rhenium Needles (Control): A lot of 8,000 8 mil tungsten-rhenium BV175-8 needles were prepared in the same manner as the non-barrel-coated needles in Example 1A.

Barrel-Coated Steel Needles: A lot of 8,000 8 mil steel BV175-8 needles were prepared in the same manner as the barrel-coated steel needles in Example 1A.

Testing

Test A: Visual testing was performed on the barrel-coated tungsten-rhenium needles in which 300 needles were visually scanned, using the human eye, for silicone related defects. No visual silicone related defects were determined.

Test C: Barrel drag force testing was performed on the barrel-coated tungsten-rhenium BV175-8 needles (Test C1), the non-barrel coated tungsten-rhenium BV175-8 needles (Test C2), and barrel-coated steel BV175-8 needles (Test C3). For each test, the barrels of the 30 needles are individually passed through the media. The maximum force is recorded during the pass using a Chatillon gauge and used as a measure of the barrel drag performance. The results are illustrated in Table 7 below.

TABLE 7

Measured Drag Force Results

| Sample | Maximum Drag Force (g) |
|---|---|
| Barrel-Coated Tungsten-rhenium BV175-8 Needles | 36 |
| Non-Barrel Coated Tungsten-rhenium BV175-8 Needles (Control) | 78 |
| Barrel-Coated Steel BV175-8 Needles | 32 |

As can be seen in table 7, the maximum barrel drag force of the barrel-coated tungsten-rhenium BV175-8 needles (Test C1) was found to be lower than the maximum barrel drag force of the control non-barrel coated tungsten-rhenium BV175-8 needles (Test C2). Further, the maximum barrel drag performance of the barrel-coated tungsten-rhenium BV175-8 needles (Test C1) was found to be comparable to the maximum barrel drag force of the barrel-coated steel BV175-8 needles (Test C3).

Comparative Example 3A

Barrel-Coated Tungsten-Rhenium Needles: A lot of 2,000 8 mil tungsten-rhenium BV175-8 needles were prepared similar to barrel-coated tungsten-rhenium needles in Example 1A, except that the top coating composition was a 2.75% Nusil® MED 4162 heptane solution, and the fully coated needles were cured at 110° C. for 3 hours.

Non-Barrel-Coated Tungsten-Rhenium Needles (Control): A lot of 8,000 8 mil tungsten-rhenium BV175-8 needles were prepared in the same manner as the non-barrel-coated needles in Example 1A.

Barrel-Coated Steel Needles: A lot of 8,000 8 mil steel BV175-8 needles were prepared in the same manner as the barrel-coated steel needles in Example 1A.

Testing

Test A: Visual testing was performed on the barrel-coated tungsten-rhenium needles in which 300 needles were visually scanned, using the human eye, for silicone related defects. Twenty-two needles were determined to have silicone related defect(s).

Test C: Barrel drag force testing was performed on the barrel-coated tungsten-rhenium BV175-8 needles (Test C1), the non-barrel coated tungsten-rhenium BV175-8 needles (Test C2), and barrel-coated steel BV175-8 needles (Test C3). For each test, the barrels of the 30 needles are individually passed through the media. The maximum force is recorded during the pass using a Chatillon gauge and used as a measure of the barrel drag performance. The results are illustrated in Table 8 below.

TABLE 8

Measured Drag Force Results

| Sample | Maximum Drag Force (g) |
|---|---|
| Barrel-Coated Tungsten-rhenium BV175-8 Needles | 32 |
| Non-Barrel Coated Tungsten-rhenium BV175-8 Needles (Control) | 78 |
| Barrel-Coated Steel BV175-8 Needles | 32 |

As can be seen in table 8, the maximum barrel drag force of the barrel-coated tungsten-rhenium BV175-8 needles (Test C1) was found to be lower than the maximum barrel drag force of the control non-barrel coated tungsten-rhenium BV175-8 needles (Test C2). Further, the maximum barrel drag performance of the barrel-coated tungsten-rhenium BV175-8 needles (Test C1) was found to be the same as the maximum barrel drag force of the barrel-coated steel BV175-8 needles (Test C3).

Comparative Example 3B

Barrel-Coated Tungsten-Rhenium Needles: A lot of 2,000 8 mil tungsten-rhenium BV175-8 needles were prepared similar to barrel-coated tungsten-rhenium needles in Example 1A, except that the top coating composition was a 2.5% Nusil® MED 4162 heptane solution, and the fully coated needles were cured at 190° C. for 2 hours.

Non-Barrel-Coated Tungsten-Rhenium Needles (Control): A lot of 8,000 8 mil tungsten-rhenium BV175-8 needles were prepared in the same manner as the non-barrel-coated needles in Example 1A.

Barrel-Coated Steel Needles: A lot of 8,000 8 mil steel BV175-8 needles were prepared in the same manner as the barrel-coated steel needles in Example 1A.

Testing

Test A: Visual testing was performed on the barrel-coated tungsten-rhenium needles in which 300 needles were visually scanned, using the human eye, for silicone related defects. Thirty-four needles were determined to have silicone related defect(s).

Test C: Barrel drag force testing was performed on the barrel-coated tungsten-rhenium BV175-8 needles (Test C1), the non-barrel coated tungsten-rhenium BV175-8 needles (Test C2), and barrel-coated steel BV175-8 needles (Test C3). For each test, the barrels of the 30 needles are individually passed through the media. The maximum force is recorded during the pass using a Chatillon gauge and used as a measure of the barrel drag performance. The results are illustrated in Table 9 below.

TABLE 9

Measured Drag Force Results

| Sample | Maximum Drag Force (g) |
|---|---|
| Barrel-Coated Tungsten-rhenium BV175-8 Needles | 30 |
| Non-Barrel Coated Tungsten-rhenium BV175-8 Needles (Control) | 78 |
| Barrel-Coated Steel BV175-8 Needles | 32 |

As can be seen in table 9, the maximum barrel drag force of the barrel-coated tungsten-rhenium BV175-8 needles (Test C1) was found to be lower than the maximum barrel drag force of the control non-barrel coated tungsten-rhenium BV175-8 needles (Test C2). Further, the maximum barrel drag performance of the barrel-coated tungsten-rhenium BV175-8 needles (Test C1) was found to be lower than the maximum barrel drag force of the barrel-coated steel BV175-8 needles (Test C3).

Comparative Example 3C

Barrel-Coated Tungsten-Rhenium Needles: A lot of 2,000 8 mil tungsten-rhenium BV175-8 needles were prepared similar to barrel-coated tungsten-rhenium needles in Example 1A, except that the top coating composition was a 2.5% Nusil® MED 4162 heptane solution, and the fully coated needles were cured at 130° C. for 2 hours.

Non-Barrel-Coated Tungsten-Rhenium Needles (Control): A lot of 8,000 8 mil BV175-8 tungsten-rhenium needles were prepared in the same manner as the non-barrel coated needles in Example 1A.

Barrel-Coated Steel Needles: A lot of 8,000 8 mil BV175-8 steel needles were prepared in the same manner as the barrel-coated steel needles in Example 1A.

Testing

Test A: Visual testing was performed on the barrel-coated tungsten-rhenium needles in which 300 needles were visually scanned, using the human eye, for silicone related defects. Sixteen needles were determined to have silicone related defect(s).

Test C: Barrel drag force testing was performed on the barrel-coated tungsten-rhenium BV175-8 needles (Test C1), the non-barrel coated tungsten-rhenium BV175-8 needles (Test C2), and barrel-coated steel BV175-8 needles (Test C3). For each test, the barrels of the 30 needles are individually passed through the media. The maximum force is recorded during the pass using a Chatillon gauge and used as a measure of the barrel drag performance. The results are illustrated in Table 10 below.

TABLE 10

Measured Drag Force Results

| Sample | Maximum Drag Force (g) |
| --- | --- |
| Barrel-Coated Tungsten-rhenium BV175-8 Needles | 36 |
| Non-Barrel Coated Tungsten-rhenium BV175-8 Needles (Control) | 78 |
| Barrel-Coated Steel BV175-8 Needles | 32 |

As can be seen in the table 10, the maximum barrel drag force of the barrel-coated tungsten-rhenium BV175-8 needles (Test C1) was found to be lower than the maximum barrel drag force of the control non-barrel coated tungsten-rhenium BV175-8 needles (Test C2). Further, the maximum barrel drag performance of the barrel-coated tungsten-rhenium BV175-8 needles (Test C1) was found to be comparable to the maximum barrel drag force of the barrel-coated steel BV175-8 needles (Test C3).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety. Any patent, publication, or information, in whole or in part, that is said to be incorporated by reference herein is incorporated herein only to the extent that the incorporated material does not conflict with existing definitions, statements, or other disclosure material set forth in this document. As such the disclosure as explicitly set forth herein supersedes any conflicting material incorporated herein by reference.

What is claimed is:

1. A system for coating a surgical needle, the system comprising:
    a first coating system that is configured to apply at least one of a primer coat and a base coat to a first portion of a surgical needle blank;
    a laser drilling system that is configured to create a suture attachment end within a second portion of the surgical needle blank, thereby forming a surgical needle having first and second portions that correspond to the first and second portions of the surgical needle blank, the second portion being uncoated; and
    a second coating system that is configured to apply a top coat to the first and second portions of the surgical needle, the second coating system includes a basket configured to house the surgical needle during application of the top coat, the basket having a base portion, a top portion, and a first and a second pair of opposing sidewalls each extending from the base portion to the top portion, thereby defining a total surface area of the basket, the basket having a drainage area that is from 50% to about 95% of the total surface area.

2. The system of claim 1, further comprising a first drying system that is configured to remove at least a portion of excess top coat from the surgical needle, and the drying system includes a vacuum drying chamber.

3. The system of claim 1, further comprising a second drying system that is configured to remove at a least a portion of solvent from the top coat.

4. The system of claim 1, further comprising a curing system that is configured to at least partially cure at least one of the primer coat and the base coat.

5. The system of claim 1, wherein the first coating system is a spray coating system.

6. The system of claim 1, wherein the base portion includes a porous substrate that is configured to retain the surgical needle within the basket and allow at least a portion of excess top coat to pass therethrough.

7. The system of claim 6, wherein the top portion includes a porous substrate that is configured to allow air to pass therethrough.

8. The system of claim 7, wherein each sidewall has an inner surface and an outer surface with one or more drainage holes extending therebetween, the one or more drainage holes being configured to allow at least a portion of excess top coat to pass therethrough, and wherein the one or more drainage holes remain open when the top portion is in contact with the inner surfaces.

9. The system of claim 1, wherein the surgical needle blank is formed from a tungsten-rhenium alloy.

10. The system of claim 1, wherein the suture attachment end is a bore hole.

11. A system for coating a surgical needle, the system comprising:
    a surgical needle blank having a first portion and a second portion, the first portion being coated with at least one first coating and the second portion being uncoated;
    a laser drilling system that is configured to create a suture attachment end within a second portion of the surgical needle blank, thereby forming a surgical needle having first and second portions that correspond to the first and second portions of the surgical needle blank; and
    a first coating system that is configured to apply a second coating to at least the second portion of the surgical needle, the first coating system includes a basket configured to house the surgical needle during application of the second coating, the basket having a drainage area that is from 50% to about 95% of a total surface area of the basket.

12. The system of claim 11, wherein the at least one first coating comprises at least one of a primer coat and a base coat.

13. The system of claim 11, further comprising a second coating system that is configured to apply the at least one first coating to the first portion of the surgical needle blank.

14. The system of claim 13, wherein the second coating system is a spray coating system.

15. The system of claim 11, further comprising a first drying system that is configured to remove at least a portion of excess second coating from the surgical needle, and the drying system includes a vacuum drying chamber.

16. The system of claim 11, further comprising a second drying system that is configured to remove at a least a portion of solvent from the second coating.

17. The system of claim 11, further comprising a curing system that is configured to at least partially cure the first coating.

18. The system of claim 11, wherein the surgical needle blank is formed from a tungsten-rhenium alloy.

19. The system of claim 11, wherein the suture attachment end is a bore hole.

\* \* \* \* \*